United States Patent [19]

Lehnhardt et al.

[11] Patent Number: 5,426,219

[45] Date of Patent: Jun. 20, 1995

[54] PROCESS FOR RECOVERING ORGANIC ACIDS

[75] Inventors: William F. Lehnhardt; Robert V. Schanefelt; Lori L. Napier, all of Decatur, Ill.

[73] Assignee: A.E. Staley Manufacturing Co., Decatur, Ill.

[21] Appl. No.: 96,939

[22] Filed: Jul. 26, 1993

[51] Int. Cl.⁶ ............................................... C07C 51/42
[52] U.S. Cl. ................................... 562/580; 562/578; 562/589; 562/593
[58] Field of Search ................. 562/580, 589, 578, 593

[56] References Cited

U.S. PATENT DOCUMENTS

| | | |
|---|---|---|
| 686,170 | 11/1991 | Waite . |
| 2,223,797 | 12/1940 | Tindall ................. 260/535 |
| 2,710,880 | 6/1955 | Filachione et al. ............ 260/535 |
| 3,944,606 | 3/1976 | Rieger et al. ............ 260/535 P |
| 4,275,234 | 6/1981 | Baniel et al. ............ 562/584 |
| 4,334,095 | 6/1982 | Baniel ................. 562/584 |
| 4,444,881 | 4/1984 | Urbas ................. 435/139 |
| 4,698,303 | 10/1987 | Bailey et al. ............ 435/139 |
| 4,771,001 | 9/1988 | Bailey et al. ............ 435/139 |
| 4,963,486 | 10/1990 | Hang ................. 435/139 |
| 5,068,418 | 11/1991 | Kulprathipanja et al. ......... 562/580 |
| 5,079,164 | 1/1992 | Kirkovits et al. ............ 435/139 |
| 5,089,664 | 2/1992 | Dalcanale et al. ............ 562/580 |
| 5,104,492 | 4/1992 | King et al. ............ 203/15 |
| 5,210,294 | 5/1993 | Mantovani et al. ............ 562/580 |
| 5,210,296 | 5/1993 | Cockrem et al. ............ 562/589 |

FOREIGN PATENT DOCUMENTS

| | | |
|---|---|---|
| 0375463 | 12/1989 | European Pat. Off. . |
| 0393818 | 2/1990 | European Pat. Off. . |
| 0517242 | 12/1992 | European Pat. Off. . |
| WO93/00440 | 1/1993 | WIPO . |
| WO93/06226 | 4/1993 | WIPO . |

OTHER PUBLICATIONS

Dietz et al, "Physical Properties of Sodium, Potassium, and Ammonium Lactate Solutions," Industrial and Engineering Chemistry, 33:11, pp. 1444–1447 (Nov. 1941).
Pan et al, "Purification of Lactic Acid for Fermentation of Corn Products," Chemical Abstracts 113:96160c (1990).
Czytko et al, "Continuous Glucose Fermentation for Lactic Acid Production Recovery of Acid by Electrodialysis," Chemical Abstracts 112:117239g (1990).
Eveleva et al, "Lactic Acid," Chemical Abstracts 111:132518v (1989).

(List continued on next page.)

Primary Examiner—José G. Dees
Assistant Examiner—Barbara S. Frazier
Attorney, Agent, or Firm—Arnold, White & Durkee

[57] ABSTRACT

An organic acid can be recovered from a fermentation broth by clarifying the broth to remove at least a substantial portion of the impurities therein, producing a clarified feed; acidulating the clarified feed by adding a quantity of a mineral acid effective to lower the pH of the feed to between about 1.0 and about 4.5, producing an acidulated feed which is substantially saturated with respect to at least one electrolyte selected from the group consisting of $MHSO_4$, $M_2SO_4$, $M_3PO_4$, $M_2HPO_4$, $MH_2PO_4$, and $MNO_3$, where M is selected from the group consisting of Na, $NH_4$, and K; extracting the acidulated feed with an extraction mixture which includes (a) water, (b) a mineral acid, in a quantity effective to maintain the pH of the feed between about 1.0 and about 4.5, and (c) an oxygenated solvent which has limited miscibility with water and the acidulated feed, the oxygenated solvent having from 4 to 12 carbon atoms and having at least one functional group selected from the group consisting of hydroxyl, ester, keto, ether, carbonyl, and amido, with the extraction producing a solvent extract and a first raffinate; and back extracting the solvent extract with an aqueous liquid, thereby producing an organic acid-rich aqueous extract and an organic acid-depleted solvent raffinate.

33 Claims, 10 Drawing Sheets

OTHER PUBLICATIONS

Obara, "Purfication of Lactic Acid from Fermentation Broth," Chemical Abstracts 111:76553p (1989).

Obara, "Purification of Organic Acid from Fermentation Fluid and Apparatus Therefor," Chemical Abstracts 111:22197g (1989).

Ono et al, "Separation of Lactic Acid by Extraction with Isopropyl Acetate," Chemical Abstracts 110:172707s (1989).

Maenato et al, "Separation and Purification of Lactic Acid," Chemical Abstracts 107:115250b (1987).

Daicel Chemical Industries, Ltd., "Purification of Lactic Acid," Chemical Abstracts 95:203332u (1981).

Griffith et al, "Continuous Lactic Acid Production Using a Fixed-Film System," Chemical Abstracts 92:58182b (1980).

Napierala et al, "Production of Alimentary Lactic Acid of High Purity," Chemical Abstracts 78:135586b (1973).

Vogt et al, "Continuous Recovery of Pure Lactic Acid," Chemical Abstracts 75:117972h (1971).

Chaintron, "Purification of Lactic Acid," Chemical Abstracts 74:41925b (1971).

Boroda et al, "Purification and Concentration of Lactic Acid," Chemical Abstracts 70:67528s (1969).

Colin et al, "Extraction of Organic Acids," Chemical Abstracts 69:42459y (1968).

Robatel Inc. proposal (Mar. 3, 1993).

Ono, "Purification of lactic acid with activated carbon," Chemical Abstacts 110:74833k (1989).

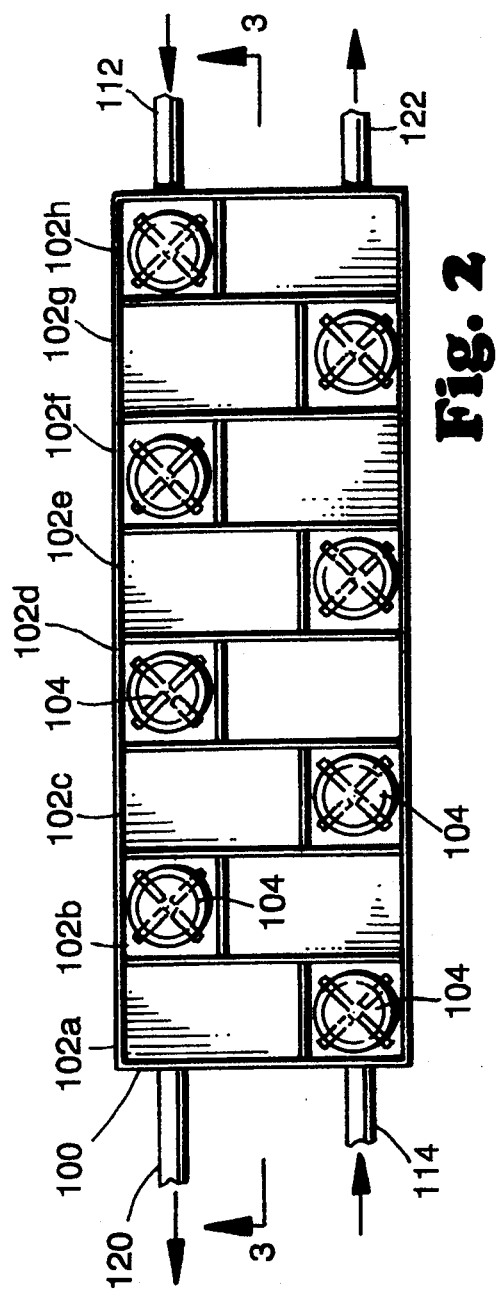
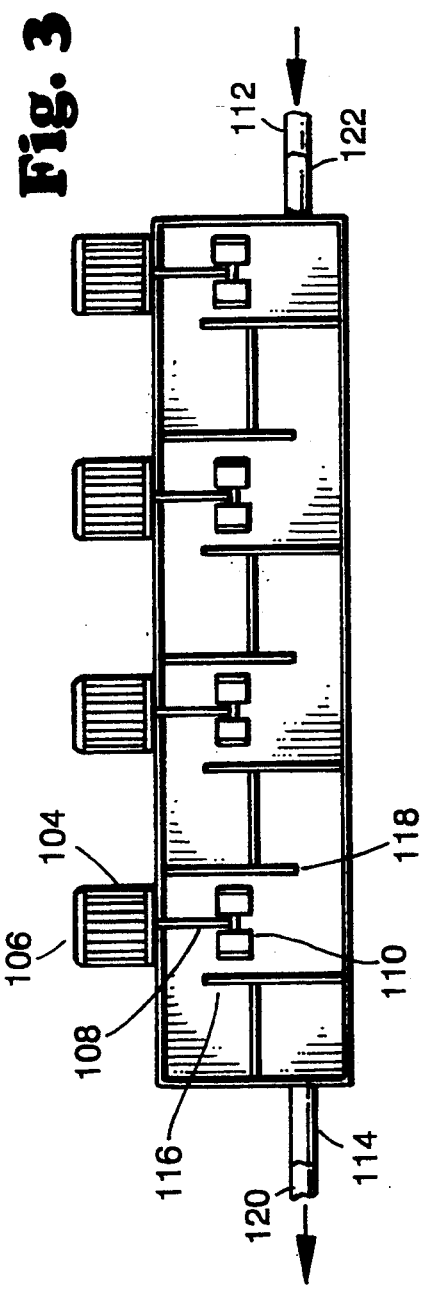

PROCESS FOR RECOVERING ORGANIC ACIDS

FIELD OF THE INVENTION

The present invention relates to a process for recovering organic acids, such as lactic acid, from fermentation broths by means of extraction.

BACKGROUND OF THE INVENTION

Lactic acid is an organic acid that has a number of commercial uses, for example in food manufacturing, pharmaceuticals, plastics, textiles, and as a starting material in various chemical processes. Lactic acid is commonly produced by fermentation of sugars, starch, or cheese whey, using microorganisms such as *Lactobacillus delbrueckii* to convert monosaccharides such as glucose, fructose, or galactose, or disaccharides such as sucrose or lactose, into lactic acid. The broth that results from the fermentation will contain unfermented sugars, carbohydrates, amino acids, proteins, and salts, as well as lactic acid. Some of these materials cause an undesirable color. The lactic acid must be recovered from the fermentation broth before it can be put to any substantial use.

A number of processes have been developed in the past to recover lactic acid or other organic acids from fermentation broths. Some of these processes involve precipitation of salts followed by decomposition of the salts, or extraction with certain organic solvents or water-insoluble amines.

For example, in Baniel U.S. Pat. No 4,275,234, an acid is recovered from an aqueous solution by extracting the solution with a water-immiscible organic extractant which comprises at least one secondary or tertiary amine dissolved in a water-immiscible organic solvent. The resulting organic extract is separated from the residual aqueous liquid, and subjected to a stripping operation with an aqueous liquid for back-extracting at least a substantial part of the acid from the organic extract into the water, while leaving substantially all of the amine in the organic phase.

In King U.S. Pat. No. 5,104,492, a carboxylic acid is recovered from an aqueous solution by contacting the aqueous solution with a substantially water-immiscible but water-wettable organic solvent. Two phases are formed, one a carboxylic acid-depleted aqueous raffinate and the other a carboxylic acid enriched water-wet solvent extract. The phases are then separated and the carboxylic acid-enriched water-wet solvent extract is dewatered. This dewatering decreases the solubility of the acid in the extract solvent and generates a carboxylic acid-containing bottoms product from which the acid can be recovered as a precipitate.

However, the recovery processes which have been used in the past have tended to be relatively expensive, because of having a large number of steps, poor efficiency of recovery, or for other reasons. Therefore, a need exists for improved processes for recovery of lactic acid and other organic acids, which can provide desirable efficiency of recovery at a reduced cost.

SUMMARY OF THE INVENTION

The present invention relates to a process for the extraction of an organic acid from an aqueous solution thereof which comprises contacting such solution with a mixture of (a) water, (b) a mineral acid in a quantity effective to maintain the pH of the mixture between about 1.0 and about 4.5, and (c) an oxygenated solvent which has limited miscibility with water and the acidulated feed, the oxygenated solvent having from 5 to 12 carbon atoms and having at least one functional group selected from the group consisting of hydroxyl, ester, keto, ether, carbonyl, and amido.

In another embodiment, the invention involves a process for recovering an organic acid which includes providing an aqueous feed containing an organic acid and impurities, and clarifying the aqueous feed to remove at least a substantial portion of the impurities therein, producing a clarified feed. In this context, "at least a substantial portion" means that at least about 10% by weight of the impurities that are present are removed. The feed can optionally be subjected to microfiltration and/or nanofiltration. The clarified liquid feed is acidulated by adding a quantity of a mineral acid effective to lower the pH of the feed to between about 1.0 and about 4.5, producing an acidulated feed which is substantially saturated with respect to at least one electrolyte selected from the group consisting of $MHSO_4$, $M_2SO_4$, $M_3PO_4$, $M_2HPO_4$, $MH_2PO_4$, and $MNO_3$, where M is selected from the group consisting of Na, $NH_4$, and K.

Next, the acidulated feed is extracted with a solvent extraction mixture which includes (a) water, (b) a mineral acid, in a quantity effective to maintain the pH of the feed between about 1.0 and about 4.5, and (c) an oxygenated solvent (such as hexanol) which has limited miscibility with water and the acidulated feed, the oxygenated solvent having from 5 to 12 carbon atoms and having at least one functional group selected from the group consisting of hydroxyl, ester, keto, ether, carbonyl, and amido, with the extraction producing a solvent extract and a first raffinate. Then the solvent extract is back extracted with an aqueous liquid, thereby producing an organic acid-rich aqueous extract and an organic acid-depleted solvent raffinate.

The process can further comprise concentrating the organic acid-rich aqueous extract by removing water and solvent; and carbon-treating the extract to remove at least a portion of the impurities remaining therein.

In another embodiment the process can further comprise recovering solvent from the first raffinate by stripping solvent therefrom; and recycling the recovered solvent for use in extracting the acidulated feed. In a variation on this particular embodiment, the pH of the acidulated feed can be maintained during the extraction at a level effective to prevent substantial precipitation of phosphate, sulfate, nitrate, and chloride salts during the extraction (e.g., pH between about 1.0 and about 4.5, and preferably between about 1.0 and about 3.5); and phosphate, sulfate, nitrate, or chloride salts can be recovered from the first raffinate by evaporation after the solvent is stripped therefrom. In this context, "level effective to prevent substantial precipitation" means that no more than de minimis precipitation will occur.

In another embodiment, an aqueous salt can be recovered by crystallizing a phosphate, sulfate, or nitrate salt from the acidulated feed; washing the crystallized salt with an aqueous liquid, preferably water; and drying the washed, crystallized salt.

In one preferred embodiment, the aqueous feed is further clarified prior to acidulation by filtering the aqueous feed to remove undesirable impurities; concentrating the feed by removing a portion of the water therein; and decolorizing the feed by contacting it with a decolorizing agent. The decolorizing agent can be granular carbon, powdered carbon, or a decolorizing resin.

In another embodiment of the invention, a second solvent extraction step is added. In particular, after extracting the acidulated feed with the extraction mixture of water, mineral acid, and oxygenated solvent, and before back extracting the solvent extract with the aqueous liquid, an additional extraction is performed in which an aqueous solution which contains a quantity of the organic acid is used as the extractant of the solvent extract from the first extraction step, thereby producing a second raffinate and a purified solvent extract, with the latter subsequently being back extracted as specified above. The second raffinate can be recycled into the acidulated feed.

The quantity of the organic acid in the aqueous extraction of the oxygenated solvent is preferably adjusted such that there is no net change in the concentration of the organic acid in the aqueous or the oxygenated solvent phase at equilibrium.

In a particularly preferred embodiment of the present invention, the process comprises:
  providing an aqueous feed containing lactic acid and impurities;
  clarifying the aqueous feed to remove at least a substantial portion of the impurities therein, producing a clarified feed;
  filtering the clarified feed to remove undesirable impurities;
  concentrating the feed by removing a portion of the water therein;
  decolorizing the feed by contacting it with a decolorizing agent;
  acidulating the clarified feed by adding a quantity of a mineral acid effective to lower the pH of the feed to between about 1.0 and about 4.5, producing an acidulated feed which is substantially saturated with respect to at least one electrolyte selected from the group consisting of $MHSO_4$, $M_2SO_4$, $M_3PO_4$, $M_2HPO_4$, $MH_2PO_4$, and $MNO_3$, where M is selected from the group consisting of Na, NH, and K;
  extracting the acidulated feed with an extraction mixture which includes (a) water, (b) a mineral acid, in a quantity effective to maintain the pH of the feed between about 1.0 and about 4.5, and (c) hexanol, with the extraction producing a first hexanol extract and a first raffinate;
  extracting the first hexanol extract with an aqueous lactic acid solution, thereby producing a second raffinate and a purified hexanol extract;
  back extracting the purified hexanol extract with an aqueous liquid, thereby producing a lactic acid-rich aqueous extract and a lactic acid-depleted hexanol raffinate;
  recovering hexanol from the first raffinate by stripping hexanol therefrom;
  recycling the recovered hexanol for use in extracting the acidulated feed;
  concentrating the lactic acid-rich aqueous extract by removing water; and
  carbon-treating the concentrated extract to remove at least a portion of the impurities remaining therein.

Additionally, a portion of the lactic acid-rich aqueous extract may be recycled to be used as the aqueous lactic acid solution to extract the first hexanol extract.

The organic acids which may be recovered by the process of the present invention include mono-, di-, and tricarboxylic acids comprised of 3-8 carbon atoms. Examples include, but are not limited to, lactic acid, citric acid, malic acid, maleic acid, fumaric acid, adipic acid, succinic acid, tartaric acid, α-ketoglutaric acid, and oxaloacetic acid.

One advantage of the present invention relates to performing the extraction at saturation, or substantially saturated conditions (e.g., $\geq 90\%$ of saturation) with the appropriate salt of the mineral acid used for the acidulation. The higher the salt concentration, the higher is the driving force for extraction of the lactic acid into the hexanol phase.

Other advantages include the use of various recycle streams which tend to minimize the number of effluent streams. Further, working at higher concentrations of lactic acid reduces the volumes of and number of extraction stages. Thus, the present invention has advantages of simplicity, reduced cost, and reduced effluent compared to the prior art.

BRIEF DESCRIPTION OF THE DRAWINGS

FIG. 2 is a plan view of a mixer-settler apparatus that can be used in the process of the present invention.

FIG. 3 is a side cross sectional view of the mixer-settler of FIG. 2, taken along axis X—X.

DETAILED DESCRIPTION OF SPECIFIC EMBODIMENTS

The term lactic acid is used in this patent to include either optical isomer of lactic acid, as well as racemic mixtures of those optical isomers. Further, it includes mixtures of lactic acid monomers, dimers, trimers, and other lactic acid polymers of low molecular weight (generally below about 740 m.w.; e.g. a polymer of about DP 10).

Figure 1:
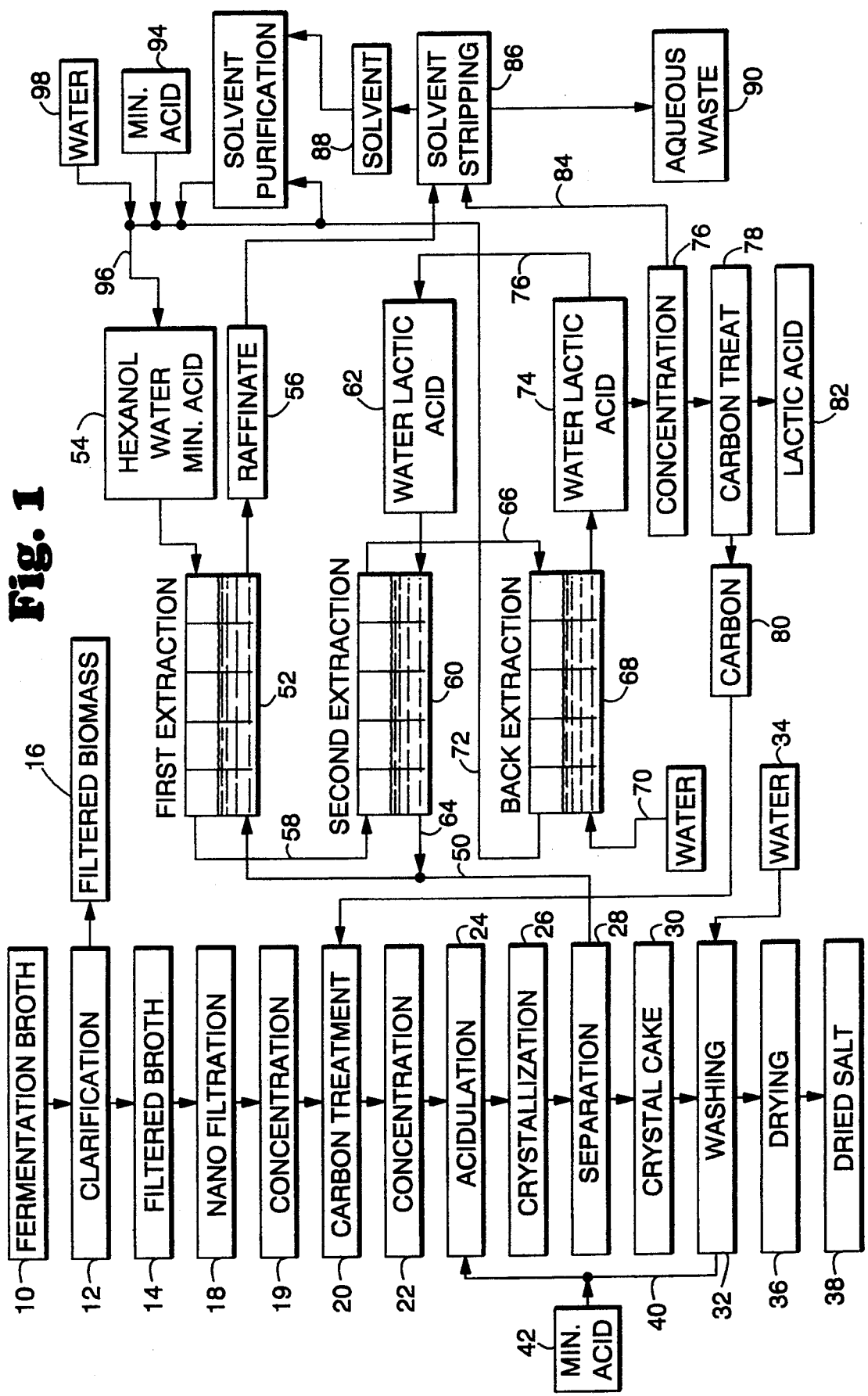
FIG. 1 is a process flow diagram for a particular embodiment of the present invention.

FIG. 1 shows a particular embodiment of a process in accordance with the present invention. Lactic acid can initially be prepared by fermentation as is known in the art. An aqueous solution containing lactic acid, in particular a fermentation broth 10, is the result of that process, and the feed for the present process.

Although the specific process embodiment of the invention described in this patent recovers lactic acid from a fermentation broth, the present invention is not limited to recovering the products of fermentation. The process of the present invention can be used in any situation where an organic acid is to be recovered from an aqueous solution or dispersion. For example, the process can be used to recover lactic acid from aqueous solutions of lactic acid-containing biopolymers, after performing the necessary process steps to free the lactic acid from the biopolymer.

The broth 10 will typically contain less than 25% by weight lactic acid. Preferably at least 80% by weight of the total lactate values in the broth are present as Na, K, or NH$_4$ lactates.

The fermentation broth 10 is clarified 12 by microfiltration or other procedures such as centrifugation, filter pressing, or rotary vacuum filtration, producing a particulate-free, filtered, fermentation broth 14. The biomass 16 removed by filtration can be recycled to the fermentation bioreactor, or can be dried and used, for example, as animal feed. The filtered broth 14 is further purified by ultrafiltration and/or nanofiltration 18 to further reduce the amount of undesirable organic impurities in the broth.

An example of a filtration process that can be used is as follows: Feedstock was prepared by microfiltration of fermentation broth followed by nanofiltration of the microfiltered permeate. A 0.02 micron Membralox ceramic element from U.S. Filter was used for the microfiltration. A multi-leaf spiral wound polymeric element with a 180 MW cutoff from Desalination Systems, Inc. was used for the nanofiltration process. This cleanup procedure yielded a feedstock with about 95–99% of the material having a molecular weight less than or equal to ammonium lactate.

The broth is then concentrated by standard evaporative techniques to a solids concentration of between 50% to 85% with a lactate content of between 38% to 65% respectively. The broth is then decolorized 20, by contacting the broth with granular or powdered carbon, or a decolorizing resin. Suitable commercial products for this purpose include:

powdered carbon: Nuchar-SA, Westraco, Darco S51, ICI Chem.;

granular carbon: Calgon CPG, Americon Norit; and decolorizing resin: Dowex Optipore Adsorbent.

The broth may also be further concentrated 22, either after or before the decolorization step 20. The lactic acid concentration in the resulting solution is typically in the range of from about 30% to about 90% by weight.

The decolorized, concentrated broth is then acidulated 24 with an acid, such as H$_3$PO$_4$, H$_2$SO$_4$, HCl, or HNO$_3$, to a pH between about 1.0 and about 4.5. (Tests of acidulated broth having pH ranging from 4.3 to 3.5 showed the greatest precipitation at pH 3.5, although pH of 3.5–3.9 yielded the highest percentage of lactic acid extracted in the solvent.) At this point, the acidulated broth contains at least 35% lactic acid by weight and is substantially saturated with respect to at least one of the electrolytes MHSO$_4$, M$_2$SO$_4$, M$_3$PO$_4$, M$_2$HPO$_4$, MH$_2$PO$_4$, and MNO$_3$, where M is selected from the group consisting of Na, NH$_4$, and K.

After acidulation 24, phosphate, sulfate, and/or nitrate salts are crystallized 26, and then the salts are separated 28 from the acidulated broth by techniques typical in the industry for separation of an inorganic salt from its corresponding broth, such as solid bowl centrifugation, basket centrifugation, filtration, vacuum filtration, and the like, producing a wet crystal cake 30. The wet crystal cake 30 is then washed 32 with water 34, and dried 36 by technique typical in the industry for drying an inorganic salt, producing a dried salt 38, for example ammonium phosphate. The water used in the washing step 32 is recycled 40 back to the concentrated broth prior to acidulation 24, and can suitably be mixed with the mineral acid 42 (e.g., phosphoric acid).

The clarified, acidulated broth 50 is then subjected to a first extraction 52 with a solvent extraction mixture 54 which includes, and preferably consists essentially of, (a) water, (b) a mineral acid, and (c) an oxygenated organic solvent. The oxygenated solvent has limited miscibility with water and the acid broth, preferably has between about 5 and about 12 carbon atoms, and carries at least one functional group selected from the group consisting of hydroxyl, ester, keto, ether, carbonyl, and amido. The oxygenated solvent more preferably has 6–8 carbon atoms. An especially preferred solvent is hexanol. The ratio of the solvent mixture 54 to the acidulated broth 50 is preferably between about 3/1 and about 6/1 by weight, preferably about 4/1.

Limiting condition extractions with the solvents hexanol, butanol, butyl acetate, isopropyl ether, 3-methyl-1-butanol, dodecanol, octanol, hexanes, and heptanol gave the following findings: butanol did not phase separate, 3-methyl-1-butanol required an equal weight addition of solvent to do so, and hexanol removed the largest quantity of lactic acid under limiting conditions.

As an example of the limited miscibility of the oxygenate organic solvent with water, Lactic Acid, Properties and Chemistry of Lactic Acid and Derivatives, by C. H. Holten, Verlag Chimie (1971), at pages 43 and 45 (which is incorporated here by reference), indicates that at 25° C. the solubility of water in 1-hexanol is 7.9% and the solubility of hexanol in water is 0.5%.

The use of acid in the oxygenated organic solvent keeps the pH in a range where the lactic acid is primarily in acid form rather than salt form. As the pH goes up, a greater percentage of the lactic acid converts to the salt form, which is much less soluble in hexanol. It is preferred to keep the amount of lactic acid in the salt form at less than 30%, which indicates that the pH should preferably be kept below 3.5.

If phosphoric acid is used in the solvent extraction mixture, there is a tendency for increased salt formation and thus an increased chance of precipitation. Using a different acid such as hydrochloric acid can reduce the chance of precipitation, because ammonium chloride is formed rather than ammonium dihydrogen phosphate, the latter already being at a saturation level. However, the use of an additional acid is not entirely desirable, and it may be preferably to use other methods of reducing or eliminating precipitation.

The amount of water in the mixture 54 is preferably that of substantial saturation (i.e., at least 90% saturated), and is most preferably that of saturation. A portion of this stream will come from a back extraction step 68 and will thus carry water at a saturation level. The addition of the phosphoric acid 94 will also carry some water with it since the phosphoric acid in preferably at 75% concentration, but the addition of the phosphate will allow an increase in the quantity of water that the hexanol will hold. The acid is added in an amount effective to maintain the pH of the broth between about 1.0 and about 4.5 during the first extraction 52, in order to optimize the extraction efficiency.

Examples of suitable compositions for the process of the present invention are as follows:

acidulated broth at pH 3.0
  53.14% lactic
  3.52% $PO_4$
  2.55% $NH_3$
  28.83% water
hexanol extractant
  6.0% water
  0.7% $H_3PO_4$
  93.3% hexanol
aqueous phase at equilibrium
  27.67% lactic acid
  47.09% water
  0.25% hexanol
  7.71% $PO_4$
  3.56% $NH_3$
  13.72% other
organic phase at equilibrium
  8.04% lactic acid
  0.03% $PO_4$
  0.08% $NH_3$
  5.81% water
  86.26% hexanol
equilibrium ratio = 6.23/1 (solvent/aqueous)

The resulting first raffinate 56 is sent to a solvent recovery system, which will be discussed further below.

The first solvent extract 58 is then subjected to a second extraction 60 in order to purify the extract. An aqueous solution 62 is used which consists essentially of water and a limited quantity of pure lactic acid, preferably no more than about 25% lactic acid by weight. The ratio of the first solvent extract 58 to the aqueous lactic acid solution 62 is preferably between about 4/1 and about 20/1 by weight. This second extraction produces a second raffinate 64 which is recycled by combining it with the acidulated broth 50 for use in the first extraction 52. A purified, second solvent extract 66 is also produced, containing primarily solvent, lactic acid, and water.

The purified solvent extract 66 is then back extracted 68 with an aqueous liquid, preferably water 70, producing a lactic acid-depleted solvent raffinate 72 and a lactic acid-rich aqueous extract 74. The ratio of the purified solvent extract 65 to the water 70 is preferably between about 4/1 and about 10/1 by weight. A portion of the lactic acid-rich aqueous extract 74 is recycled 76 to the aqueous lactic acid solution 62 for use in the second extraction 60. The remainder of the lactic acid-rich aqueous extract 74 is concentrated 76, thus removing a condensate 84 which is sent to a solvent recovery system. Minor contaminants are then removed by a decolorizing treatment 78 with carbon or a decolorizing resin. After this treatment, used carbon 80 is recycled to the earlier decolorization step 20.

The final lactic acid solution 82 will typically have a concentration of between about 30%–90% by weight.

The lactic acid-depleted solvent raffinate 72 is recycled back to the first extraction 52, where it is combined with the necessary additional ingredients to make up the solvent extraction mixture 54. The first raffinate 56 and the condensate 84 are sent to a solvent stripper 86, which separates solvent 88 from aqueous waste 90. The aqueous waste 90, which will usually contain ammonium dihydrogen phosphate, other salts, proteinaceous materials, and carbohydrates, can be used as animal feed or fertilizer. The recovered solvent 88 is sent to a solvent purification unit 92. The solvent purification unit will preferably consist of a standard construction for the heterogeneous distillation of azeotropic liquids. Some or all of the lactic acid-depleted solvent raffinate 72 is also passed through the solvent purification unit 92. The desired amount of mineral acid 94 is added to the solvent recycle stream 96, together with a controlled amount of water 98 to complete the desired makeup of the solvent extraction mixture 54 for the first extraction 52.

The extraction steps can be carried out in batch operation or continuously, and may be conducted by any conventional liquid phase extraction method, including for example counter-current liquid-liquid extraction methods or extraction columns which are known to persons skilled in this field. Centrifugation can also be used. Additional extraction stages and/or steps can be used if desired.

In a particular embodiment of the present invention, the extraction steps are carried out in a multi-stage mixer-settler apparatus, such as the Robatel Model UX 1.1 mixer-settler (Robatel Inc., Pittsfield, Mass.). In this type of extraction apparatus, each stage includes at least a mixer and a settler. The mixer brings the solvent and the feed into intimate contact with each other. In the settler portion of each stage, a lighter phase rises to the top of the settler and overflows a weir to an adjacent stage in one direction. A heavier phase sinks to the bottom of the settler, and underflows a separate weir into a different adjacent stage in a different direction.

FIGS. 2 and 3 show one embodiment of a mixer-settler 100, containing eight stages 102a–102h. Each stage has a mixer 104 driven by a motor 106 and having a shaft 108 and a turbine 110. Solvent 112 can be fed in one end of the apparatus, while the feed 114 is fed into the other end. In each stage 102, the mixer 104 mixes the solvent and feed, and they then separate at least to some degree into phases. A lighter phase will overflow an overflow weir 116 into an adjacent chamber, while a heavier phase will underflow an underflow weir 118 into a separate chamber that is also adjacent. The ultimate result is an extract 120 and a raffinate 122.

In an alternate embodiment of the process, instead of crystallizing and separating the salt (e.g., ammonium dihydrogen phosphate) before extraction, the acidulated broth fed into the extraction would contain both lactic acid (in hydrogen form) and the phosphate salt.

The extraction would be operated so as to be borderline saturated with ammonium dihydrogen phosphate, using pH in the same range as stated above, thereby preventing any substantial precipitation of the salt during extraction. The ammonium phosphate would be recovered from the raffinate stream 56 by stripping of the hexanol, followed by evaporation, leaving the salt.

EXAMPLE 1

Figure 4:
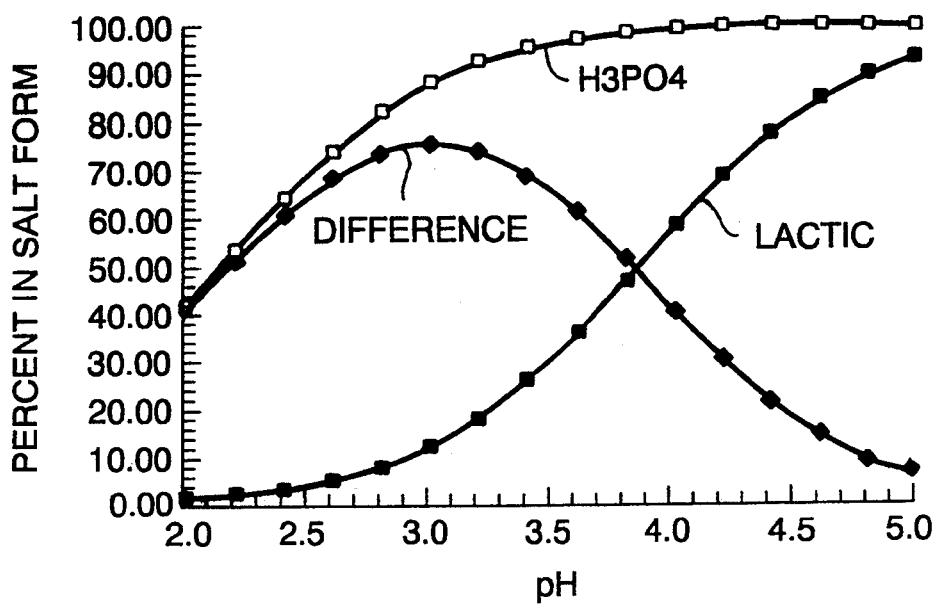
FIG. 4 is a graph of the percent of lactate and phosphate that are in salt form at different pH values, and of the difference between the percentages for the two materials.
Figure 5:
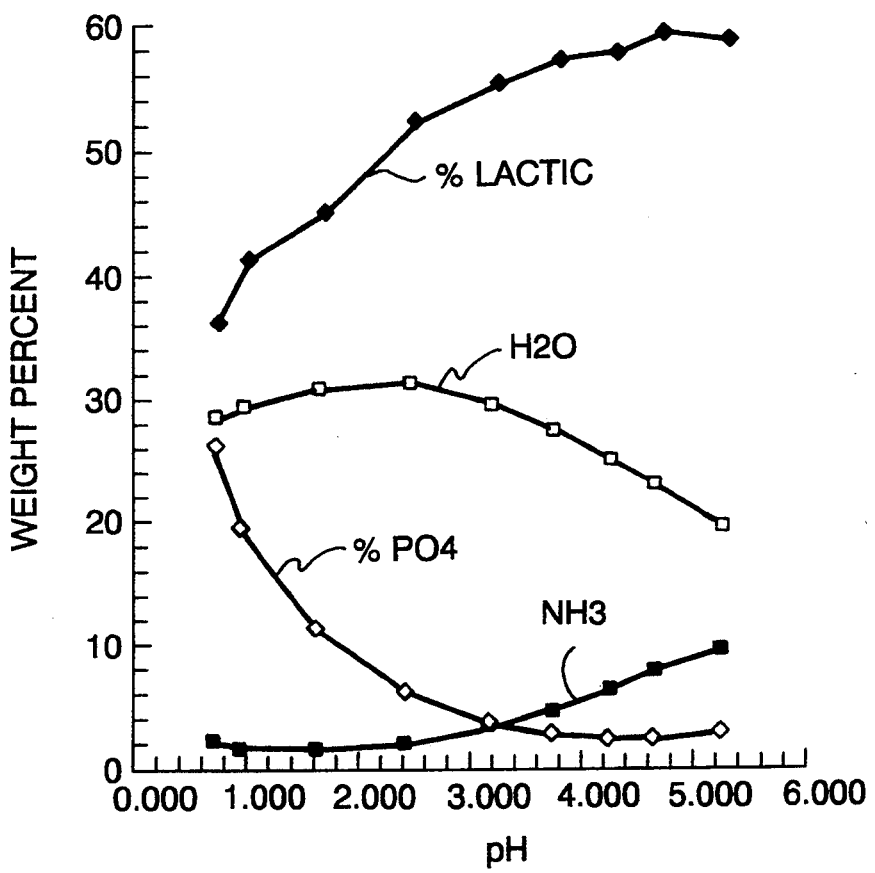
FIG. 5 is a graph of the relationship between pH and the concentration of various components in the soluble phase.
Figure 6:
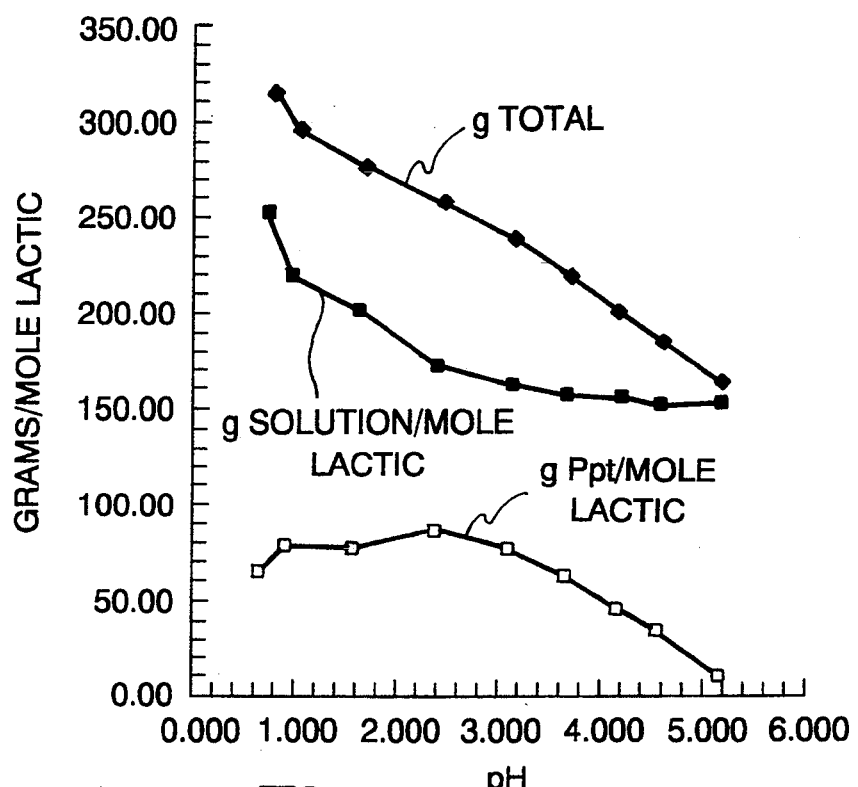
FIG. 6 is a graph of the relationship between pH and quantity of precipitate, supernatant, and total precipitate plus supernatant per mole of lactic acid.
Figure 7:
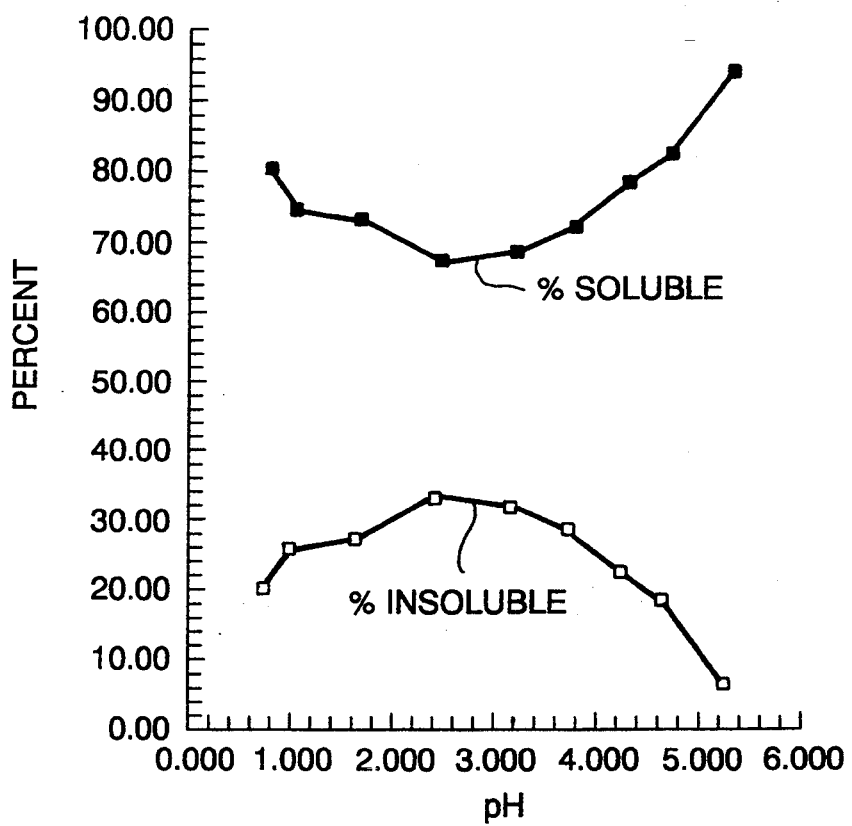
FIG. 7 is a graph of the relationship between pH and the distribution of soluble and insoluble phases.
Figure 8:
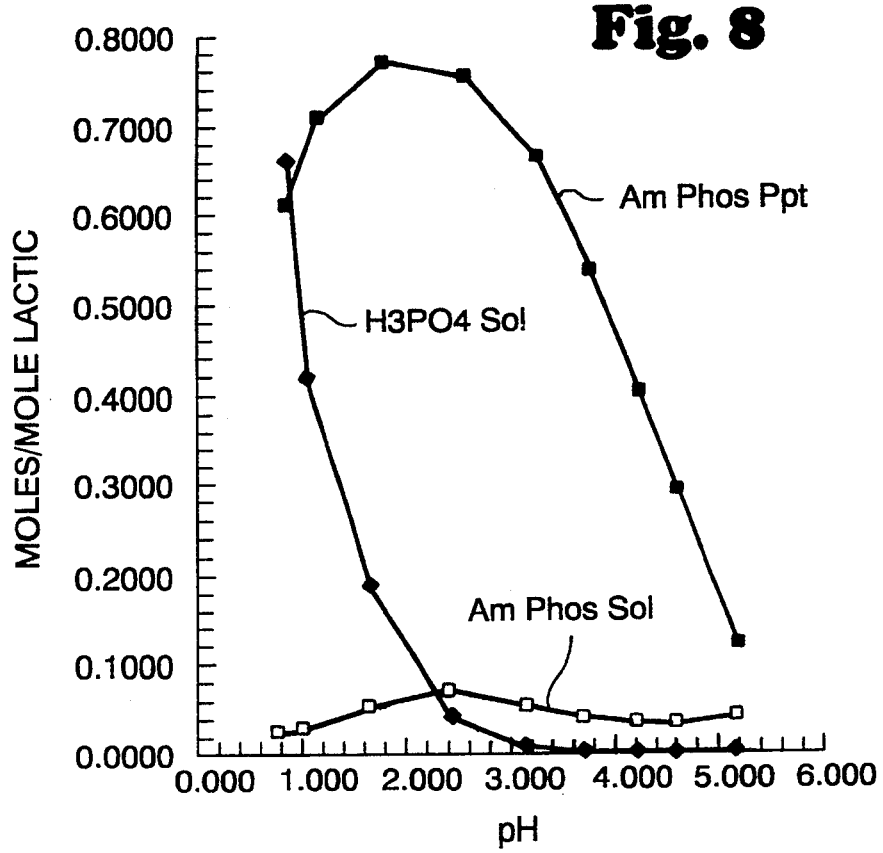
FIG. 8 is a graph of the relationship between pH and the moles of various components per mole of lactic acid.
Figure 9:
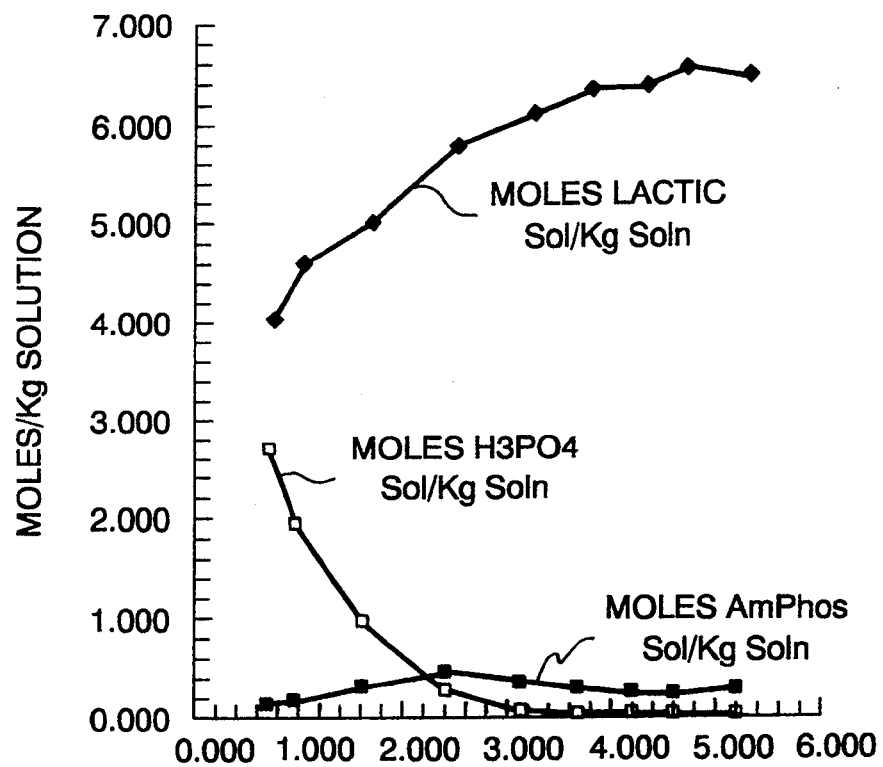
FIG. 9 is a graph of the relationship between pH and the moles of various components per kg of solution.
Figure 10:
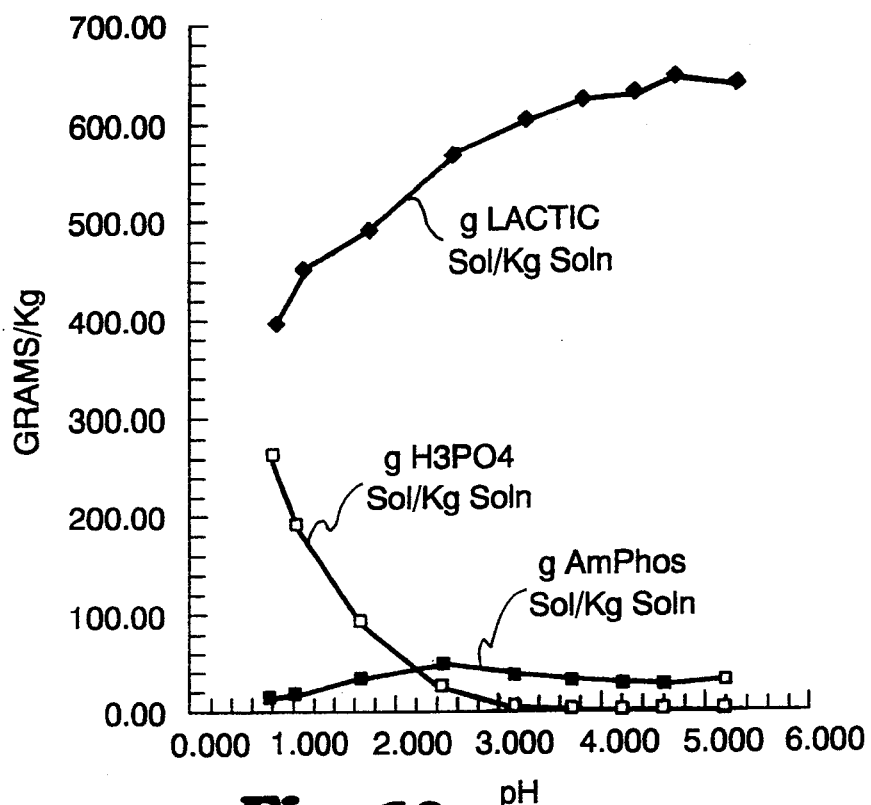
FIG. 10 is a graph of the relationship between pH and the grams of various components per kg of solution.
Figure 11:
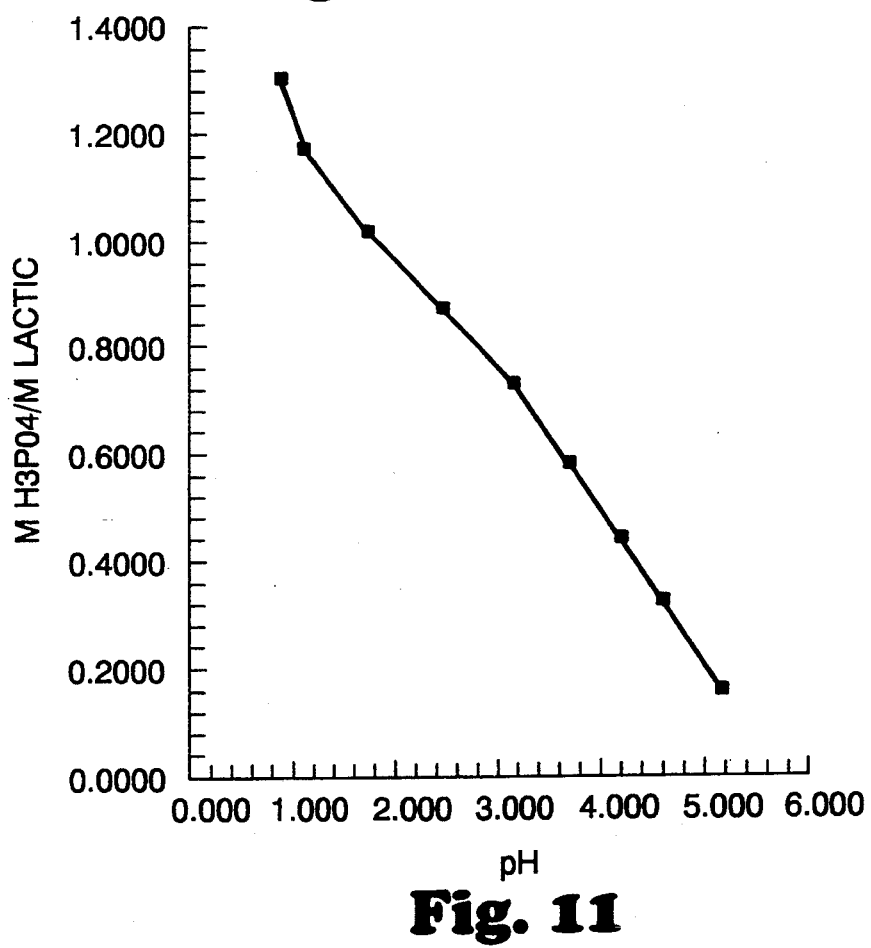
FIG. 11 is a graph of the relationship between pH and the ratio of moles of phosphoric acid to moles of lactic acid.

Calculations were performed to evaluate the pH distributions of salt and acid forms of lactic acid and phosphoric acid, using the Henderson-Hasselbach equation ($pH = pK_a + \log \text{salt/acid}$), and the following values:
lactic acid pK = 3.858
$H_3PO_4$ $pK_1 = 2.15$
The results are plotted in FIG. 4. (Note that the above equation is generally used for dilute aqueous solutions; the relationship may be slightly different in the system used here.) At pH 4.1, about 64% of lactic acid values will exist as ammonium lactate, with the remaining about 36% as acid. The difference between the lactate and phosphate curves will theoretically be the largest at a pH of about 3.0, and thus that pH may be preferable for the extraction.

EXAMPLE 2

A clarified fermentation broth was obtained, shown in Table 1 as sample 310. A quantity of broth (C) was acidulated with a quantity of 75% phosphoric acid (D) and the resulting pH was measured (B). The supernatant was removed after centrifugation and analyzed as shown (F, G, H, I). The only assumption made was that all of the lactic acid was in the soluble phase.

TABLE 1A

| A Sample No | B pH | C g Sample | D g 75% H3PO4 | E Total Wt C + D | F % NH3 Sol | G % H2O Sol | H % Lactic Sol | I % PO4 Sol | J g H3PO4 D*0.75 |
|---|---|---|---|---|---|---|---|---|---|
| 310 | 6.079 | 10.00 | 0 | 10.00 | 10.84 | 16.5 | 62.89 | 0.17 | 0.0000 |
| 311 | 5.204 | 10.00 | 1.40 | 11.40 | 9.16 | 19.2 | 58.87 | 2.41 | 1.0500 |
| 312 | 4.603 | 10.01 | 2.93 | 12.94 | 7.71 | 22.6 | 59.49 | 1.96 | 2.1975 |
| 313 | 4.204 | 10.02 | 3.98 | 14.00 | 5.95 | 24.7 | 57.93 | 2.04 | 2.9850 |
| 314 | 3.689 | 10.04 | 5.31 | 15.35 | 4.23 | 27.3 | 57.40 | 2.46 | 3.9825 |
| 315 | 3.134 | 10.03 | 6.64 | 16.67 | 2.79 | 29.5 | 55.44 | 3.28 | 4.9800 |
| 316 | 2.389 | 10.00 | 7.92 | 17.92 | 1.72 | 31.2 | 52.36 | 5.89 | 5.9400 |
| 317 | 1.600 | 10.08 | 9.33 | 19.41 | 1.43 | 30.8 | 44.86 | 11.14 | 6.9975 |
| 318 | 0.965 | 10.00 | 10.59 | 20.59 | 1.70 | 29.4 | 41.19 | 19.39 | 7.9425 |
| 319 | 0.699 | 10.01 | 11.91 | 21.92 | 1.95 | 28.3 | 35.99 | 26.24 | 8.9325 |

TABLE 1B

| A Sample No | B pH | K g Lactic C* 0.6289 | L % Lactic All Sol K* 100/E | M g Soln Calc K/H * 100 | N g Ppt Calc E − M | O Moles Lactic K/90.08 | P Moles H3PO4 J/98.0 | Q M H3PO4/M Lactic P/O |
|---|---|---|---|---|---|---|---|---|
| 310 | 6.079 | 6.2890 | 62.89 | | | 0.0698 | 0.0000 | |
| 311 | 5.204 | 6.2890 | 55.17 | 10.683 | 0.717 | 0.0698 | 0.0107 | 0.1535 |
| 312 | 4.603 | 6.2953 | 48.65 | 10.582 | 2.358 | 0.0699 | 0.0224 | 0.3209 |
| 313 | 4.204 | 6.3016 | 45.01 | 10.878 | 3.122 | 0.0700 | 0.0305 | 0.4354 |
| 314 | 3.689 | 6.3142 | 41.13 | 11.000 | 4.350 | 0.0701 | 0.0406 | 0.5798 |
| 315 | 3.134 | 6.3079 | 37.84 | 11.378 | 5.292 | 0.0700 | 0.0508 | 0.7257 |
| 316 | 2.389 | 6.2890 | 35.09 | 12.011 | 5.909 | 0.0698 | 0.0606 | 0.8682 |
| 317 | 1.600 | 6.3393 | 32.66 | 14.131 | 5.279 | 0.0704 | 0.0714 | 1.0146 |
| 318 | 0.965 | 6.2890 | 30.54 | 15.268 | 5.322 | 0.0698 | 0.0810 | 1.1609 |
| 319 | 0.699 | 6.2953 | 28.72 | 17.492 | 4.428 | 0.0699 | 0.0911 | 1.3042 |

TABLE 1C

| A Sample No | B pH | R Moles NH4H2PO4 Ppt N/115.03 | S Moles NH3 Sol F*.01*M/17.03 | T Moles PO4 Sol I*.01*M/94.97 | U Moles PO4 ppt P − T | V Salt (PO4)/Acid 10 (B −2.15) | W Moles NH4H2PO4 Sol (V*T)(1 + V) |
|---|---|---|---|---|---|---|---|
| 310 | 6.079 | | | | | | |
| 311 | 5.204 | 0.0062 | 0.0575 | 0.0027 | 0.0080 | 1132.400 | 0.0027 |
| 312 | 4.603 | 0.0205 | 0.0479 | 0.0022 | 0.0202 | 283.792 | 0.0022 |
| 313 | 4.204 | 0.0271 | 0.0380 | 0.0023 | 0.0281 | 113.240 | 0.0023 |
| 314 | 3.689 | 0.0378 | 0.0273 | 0.0028 | 0.0378 | 34.594 | 0.0028 |
| 315 | 3.134 | 0.0460 | 0.0186 | 0.0039 | 0.0469 | 9.638 | 0.0036 |
| 316 | 2.389 | 0.0514 | 0.0121 | 0.0074 | 0.0532 | 1.734 | 0.0047 |
| 317 | 1.600 | 0.0459 | 0.0119 | 0.0166 | 0.0548 | 0.282 | 0.0036 |
| 318 | 0.965 | 0.0463 | 0.0152 | 0.0312 | 0.0499 | 0.065 | 0.0019 |
| 319 | 0.699 | 0.0385 | 0.0200 | 0.0483 | 0.0428 | 0.035 | 0.0017 |

TABLE 1D

| A Sample No | B pH | X Moles H3PO4 Sol T − W | Y g Solution/ Mole Lactic M/O | Z g Ppt/Mole Lactic N/O | AA Total g/Mole Lactic Y + Z | AB % Precipitate 100*Z/AA | AC % Soluble 100*Y/AA |
|---|---|---|---|---|---|---|---|
| 310 | 6.079 | | 153.02 | | | | |
| 311 | 5.204 | 0.0000 | 153.02 | 10.27 | 163.29 | 6.29 | 93.71 |
| 312 | 4.603 | 0.0000 | 151.42 | 33.74 | 185.16 | 18.22 | 81.78 |

TABLE 1D-continued

| A Sample No | B pH | X Moles H3PO4 Sol T − W | Y g Solution/ Mole Lactic M/O | Z g Ppt/Mole Lactic N/O | AA Total g/Mole Lactic Y + Z | AB % Precipitate 100*Z/AA | AC % Soluble 100*Y/AA |
|---|---|---|---|---|---|---|---|
| 313 | 4.204 | 0.0000 | 155.50 | 44.63 | 200.13 | 22.30 | 77.70 |
| 314 | 3.689 | 0.0001 | 156.93 | 62.05 | 218.99 | 28.34 | 71.66 |
| 315 | 3.134 | 0.0004 | 162.48 | 75.58 | 238.06 | 31.75 | 68.25 |
| 316 | 2.389 | 0.0027 | 172.04 | 84.64 | 256.68 | 32.97 | 67.03 |
| 317 | 1.600 | 0.0129 | 200.80 | 75.01 | 275.81 | 27.20 | 72.80 |
| 318 | 0.965 | 0.0293 | 218.69 | 76.23 | 294.92 | 25.85 | 74.15 |
| 319 | 0.699 | 0.0467 | 250.29 | 63.36 | 313.66 | 20.20 | 79.80 |

TABLE 1E

| A Sample No | B pH | AD % Precipitate 100 - AC | AE Mol AmPhos PPT/Mol Lactic U/V | AF Mol AmPhos Sol/Mol Lactic W/O | AG Mol H3PO4 Sol/Mol Lactic X/O | AH Mole AmPhos Ppt/ Kg Soln AE *1000/Y |
|---|---|---|---|---|---|---|
| 310 | 6.079 | | | | | |
| 311 | 5.204 | 6.29 | 0.1146 | 0.0388 | 0.0000 | 0.749 |
| 312 | 4.603 | 18.22 | 0.2896 | 0.0311 | 0.0001 | 1.913 |
| 313 | 4.204 | 22.30 | 0.4020 | 0.0331 | 0.0003 | 2.585 |
| 314 | 3.689 | 28.34 | 0.5391 | 0.0395 | 0.0011 | 3.435 |
| 315 | 3.134 | 31.75 | 0.6696 | 0.0508 | 0.0053 | 4.121 |
| 316 | 2.389 | 32.97 | 0.7615 | 0.0677 | 0.0390 | 4.426 |
| 317 | 1.600 | 27.20 | 0.7791 | 0.0518 | 0.1838 | 3.880 |
| 318 | 0.965 | 25.85 | 0.7143 | 0.0274 | 0.4191 | 3.266 |
| 319 | 0.699 | 20.20 | 0.6127 | 0.0236 | 0.6679 | 2.448 |

TABLE 1F

| A Sample No | B pH | AI Mole AmPhos Sol/Kg Soln AF*1000/Y | AJ Mole H3PO4 Kg Soln AG*1000/Y | AK Mole Lactic/ Kg Soln 1*1000/Y | Al g Am Phos Sol/Kg Soln AI·115.03 | AM g H3PO4 Sol/Kg Soln AJ*98.0 | AN g Lactic Sol/Kg Soln AK*90.08 |
|---|---|---|---|---|---|---|---|
| 310 | 6.079 | | | | | | |
| 311 | 5.204 | 0.254 | 0.000 | 6.535 | 29.16 | 0.02 | 588.70 |
| 312 | 4.603 | 0.206 | 0.001 | 6.604 | 23.66 | 0.07 | 594.90 |
| 313 | 4.204 | 0.213 | 0.002 | 6.431 | 24.49 | 0.18 | 579.30 |
| 314 | 3.689 | 0.252 | 0.007 | 6.372 | 28.96 | 0.71 | 574 00 |
| 315 | 3.134 | 0.313 | 0.032 | 6.155 | 35.99 | 3.18 | 554.40 |
| 316 | 2.389 | 0.393 | 0.227 | 5.813 | 45.25 | 22.23 | 523.60 |
| 317 | 1.600 | 0.258 | 0.915 | 4.980 | 29.67 | 89.68 | 448.60 |
| 318 | 0.965 | 0.125 | 1.917 | 4.573 | 14.40 | 187.82 | 411.90 |
| 319 | 0.699 | 0.094 | 2.669 | 3.995 | 10.87 | 261.51 | 359.90 |

FIGS. 5–11 summarize the results of this experiment graphically.

EXAMPLE 3

Figure 12:
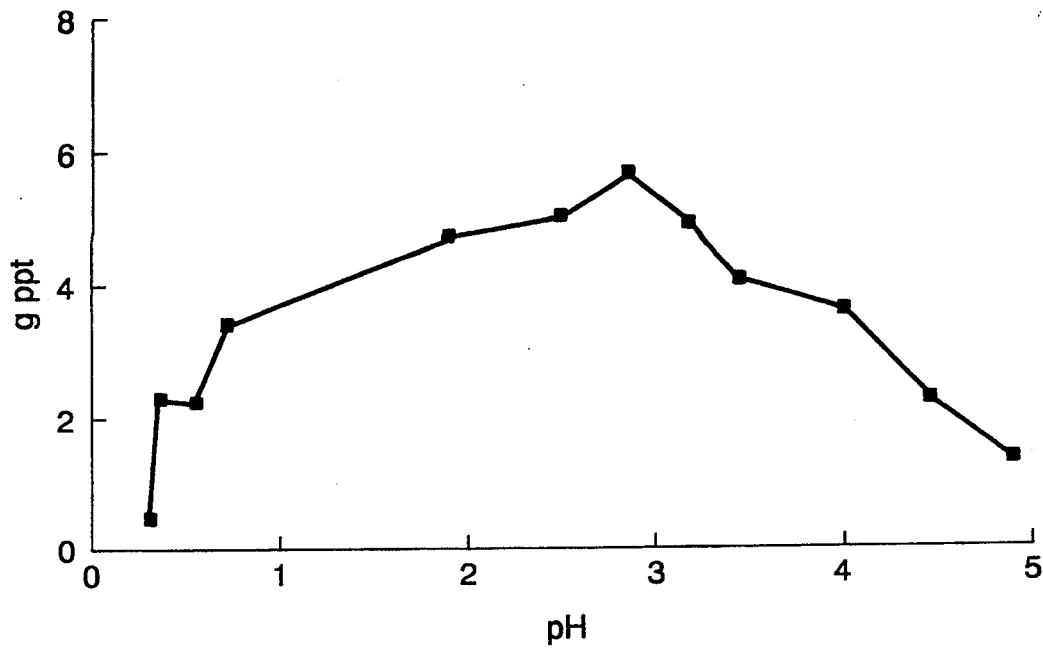
FIG. 12 is a graph of the amount of precipitate at different pH's for a broth sample acidulated with $H_2SO_4$.
Figure 13:
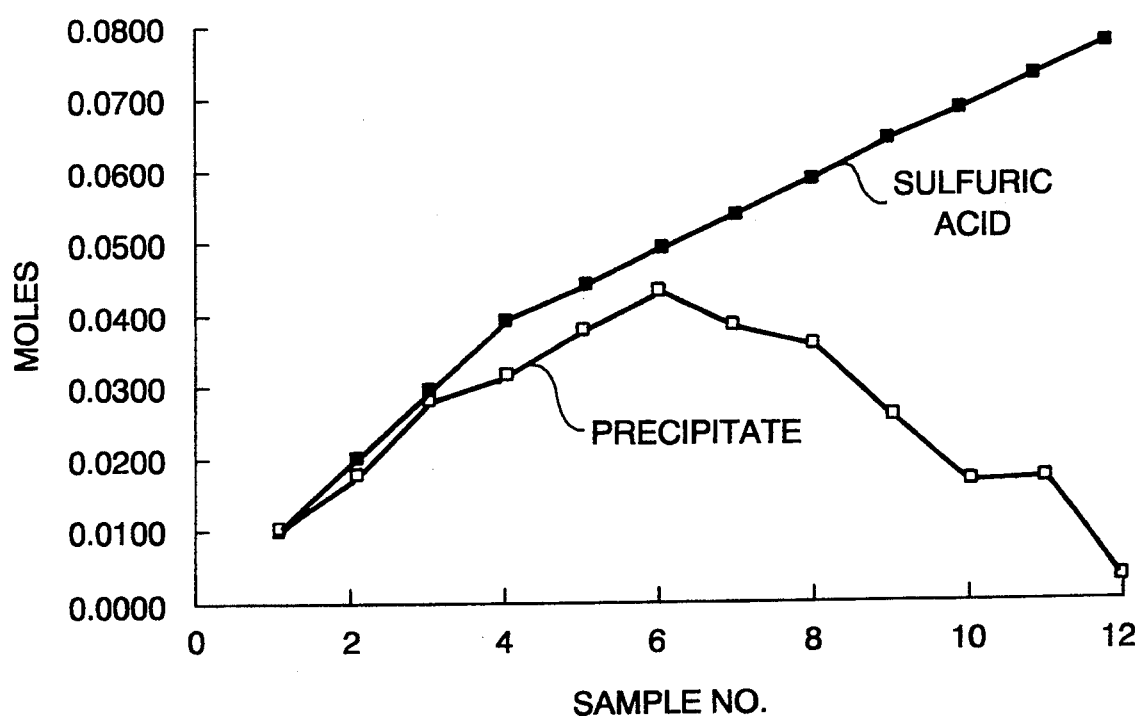
FIG. 13 is a graph of the moles of $H_2SO_4$ added and precipitate formed for different samples of acidulated broth.

Concentrated fermentation broth (containing 78.24% lactic acid, 3.18% water, 12.28% NH3, 1472 ppm PO4, and 5115 ppm Cl) was diluted with water such that the resulting lactic acid concentration was 65.41%. The pH of this diluted broth was 5.41. Portions of the broth were acidified with sulfuric acid (96.1%) such that a series of samples were produced in a pH range of 5 to 0.3. The samples were centrifuged and the supernatant was removed and analyzed for lactic acid. The only assumption made was that all of the lactic acid was in the soluble phase. See Table 2 below and FIGS. 12 and 13 for the results.

TABLE 2

| g broth | g lactic | moles lactic | g H2SO4 added (96.1%) | g H2SO4 | moles H2SO4 | g supernate | g wet ppt | pH | g ppt | g soluble | moles ammonium sulfate | cum moles |
|---|---|---|---|---|---|---|---|---|---|---|---|---|
| 20.04 | 13.026 | 0.1446 | 1 | 0.962 | 0.0098 | 16.68 | 4.36 | 4.96 | 1.35 | 19.69 | 0.010 | 0.01 |
| 20.02 | 13.013 | 0.1445 | 2.03 | 1.95 | 0.0199 | 15.25 | 6.8 | 4.51 | 2.32 | 19.73 | 0.018 | 0.028 |
| 20.03 | 13.0195 | 0.1445 | 3.02 | 2.91 | 0.0296 | 14.46 | 8.59 | 4.06 | 3.71 | 19.34 | 0.028 | 0.056 |
| 20.01 | 13.0065 | 0.1444 | 4.04 | 3.89 | 0.0396 | 14.02 | 10.03 | 3.51 | 4.18 | 19.87 | 0.032 | 0.087 |
| 20 | 13 | 0.1443 | 4.5 | 4.33 | 0.0441 | 14.65 | 9.85 | 3.23 | 5.05 | 19.45 | 0.038 | 0.126 |
| 20.01 | 13.0065 | 0.1444 | 5.03 | 4.84 | 0.0493 | 14.98 | 10.06 | 2.9 | 5.78 | 19.26 | 0.044 | 0.169 |
| 20 | 13 | 0.1443 | 5.5 | 5.29 | 0.0539 | 15.44 | 10.06 | 2.53 | 5.14 | 20.36 | 0.039 | 0.208 |
| 20.02 | 13.013 | 0.1445 | 6.05 | 5.82 | 0.0593 | 16.56 | 9.51 | 1.94 | 4.82 | 21.25 | 0.036 | 0.245 |
| 20.03 | 13.0195 | 0.1445 | 6.64 | 6.39 | 0.0651 | 17.39 | 9.28 | 0.73 | 3.46 | 23.21 | 0.026 | 0.271 |
| 20.03 | 13.0195 | 0.1445 | 7.08 | 6.81 | 0.0694 | 17.78 | 9.33 | 0.56 | 2.29 | 24.82 | 0.017 | 0.288 |
| 20 | 13 | 0.1443 | 7.56 | 7.27 | 0.0742 | 16.81 | 10.75 | 0.36 | 2.35 | 25.21 | 0.018 | 0.306 |
| 20.04 | 13.026 | 0.1446 | 8.04 | 7.73 | 0.0789 | 15.11 | 12.97 | 0.3 | 0.5 | 27.58 | 0.004 | 0.310 |

EXAMPLE 4

A concentrated feed broth was acidulated with one molar equivalent of 75% H3PO4. Water was added to dissolve salts. The pH was 2.12 and after dilution the broth contained 16.80% lactic acid. 1.13 g of hexanol was added to 81.22 g of this feed, resulting in cloudiness. The mixture was allowed to sit; no cloudiness was observed. 5.23% lactic acid was recovered from the aqueous phase. Later ca. 0.18 g of precipitate was noted in the extracted feed.

EXAMPLE 5

Several acidulated broths containing lactic acid were extracted in a cross-current process. A clarified, filtered, acidulated broth containing lactic acid designated sample 5A was extracted six times. The acidulated broth feed contained 55.03% lactic acid by weight, 3.26% $PO_4$, 4.33% $NH_3$, 30.21% water, and had a pH of 4.1. The extractant contained 100 g hexanol (95.06% by weight of the total extractant), 0.2 g of 85% $H_3PO_4$ (0.19% by weight), and 5.0 g water (4.78% by weight). This amount of water represented approximate saturation of the extractant mixture. Seven g of initial acidulated broth feed were extracted with 35 g of extractant (i.e., a 5/1 solvent/feed ratio by weight).

TABLE 3

| | | Sample 5A | | |
|---|---|---|---|---|
| Extraction pass | Feed (g) | Extractant (g) | Extract (g) | % Lactic Acid in Extract | Comments |
| 1 | 7.03 | 35.13 | 35.56 | 5.01 | |
| 2 | 5.34 | 35.07 | 35.12 | 1.36 | precipitate forming |
| 3 | 5.06 | 35.08 | 34.95 | 0.72 | more precipitate |
| 4 | 5.01 | 35.03 | 34.89 | 0.46 | |
| 5 | 4.94 | 35.07 | 34.69 | 0.31 | |
| 6 | 4.95 | 35.16 | 35.30 | 0.39 | |

The pH of the remaining aqueous phase after the sixth extraction was 5.3. The aqueous phase weighed 4.59 g and contained 12.87% lactic acid. Thus 75.5% of the lactic acid in the original feed was extracted.

It appeared that the amount of acid in the extractant was not enough to keep the pH stable during extraction, or, alternatively, that the starting pH of the acidulated broth preferably should have been lower.

Another acidulated broth containing lactic acid (designated sample 5B) was extracted. The broth prior to acidulation contained 66.09 g lactic acid (0.7337 moles) out of a total weight of 101.73 g. It was acidulated with 68.30 g of 75% $H_3PO_4$ (0.5227 moles), creating a pH of 3.0 and a temperature rise from 25° C. to 55° C.

The resulting $NH_4H_2PO_4$ was removed by centrifugation and decantation. The sediment mixture totalled 113.82 g. The amount of $NH_4H_2PO_4$ formed was calculated by using the dilution of lactic acid concept to be 48.5 g (0.422 moles). The clarified broth remaining after the salt was removed totaled 56.21 g, and was made up of 33.06% (weight) lactic acid, 3.73% $PO_4$, 2.67% $NH_3$, and 28.64% water.

The extractant was made up of 100 g hexanol (94.79% by weight of the total extractant), 0.5 g of 75% $H_3PO_4$ (0.36% by weight), and 5.0 g water (5.09% by weight). The acidulated, clarified broth was extracted six times, using 32.0 g of the extractant per cycle, in a 4/1 solvent/feed ratio by weight.

TABLE 4

| | | Sample 5B | | | |
|---|---|---|---|---|---|
| Extraction pass | Feed (g) | Extractant (g) | Extract (g) | % Lactic Acid in Extract | Comments |
| 1 | 8.08 | 32.05 | 34.85 | 8.17 | |
| 2 | 5.15 | 32.02 | 32.44 | 2.12 | |
| 3 | 4.52 | 32.05 | 32.17 | 0.92 | precipitate start |
| 4 | 4.18 | 32.08 | 31.80 | 0.60 | |
| 5 | 4.25 | 32.14 | 32.17 | 0.44 | |
| 6 | 4.12 | 32.02 | 32.02 | 0.33 | |

About 4.27 g of lactic acid was extracted out of a total of about 4.39 in the feed. Thus 97.27% of the lactic acid in the original feed was extracted.

A large amount of precipitate formed during the extraction. Also, quite a bit of liquor remained with the precipitate after separation by centrifugation. This latter problem might have been minimized if filtration had been used instead of centrifugation.

Five other extractions were performed. The extraction parameters and results are shown in Table 5 below.

TABLE 5

Cross-Current Extraction
Cumulative % Lactic Acid Collected in Solvent

| Extraction Number | Sample No. | | | | | | |
|---|---|---|---|---|---|---|---|
| | 5A | 5B | 5C | 5D | 5E | 5F | 5G |
| 1 | 45.99 | 64.92 | 40.00 | 62.50 | 73.64 | 67.12 | 88.60 |
| 2 | 58.39 | 80.64 | 49.45 | 74.55 | 86.49 | 84.67 | 99.48 |
| 3 | 64.85 | 87.47 | 60.36 | 78.12 | 89.32 | 90.52 | 100.00 |
| 4 | 68.98 | 91.80 | 68.36 | 79.68 | 90.41 | 95.63 | 100.00 |
| 5 | 71.82 | 94.99 | 72.00 | 80.57 | 91.28 | 97.87 | 100.00 |
| 6 | 75.44 | 97.50 | N/A | 81.24 | 91.72 | 98.35 | 100.00 |
| Conditions | | | | | | | |
| pH | 4.10 | 3.00 | 4.10 | 2.91 | 2.65 | 3.00 | 1.31 |
| Solvent: feed ratio | 5:1 | 4:1 | 3.4:1 | 4:1 | 4:1 | 4:1 | 4:1 |
| Solvent (Hexanol) Content | | | | | | | |
| H3PO4 | 0.16% | 0.36% | — | — | — | 0.79% | — |
| H2O | 4.78% | 4.86% | — | saturated | saturated | 6.00% | saturated |

EXAMPLE 6

Phosphoric acid, acidulated fermentation broth (comprising 53.14% lactic acid, 3.52% $PO_4$, 2.55% $NH_3$, and 28.83% water, pH 3.0) was used "as is" or diluted with water to produce a series of solutions containing ammonium dihydrogen phosphate at 100%, 98%, 95%, 93%, 90%, and 80% of saturation. A 4:1 solvent/aqueous ratio was used. The solvent/extractant was 92.79% hexanol, 6.51% water, and 0.7% phosphoric acid. Precipitate formed in the first stage for all but the 90% and 80% samples. The percentage lactic acid recovery decreased only slightly, from 65.13% at full saturation to 62.09% recovery in the 80% saturated sample.

formed with the sulfuric acid sample after the third stage and redissolved after the fifth. No precipitate formed at any stage during the hydrochloric acid run.

TABLE 6

| Sample | Satur. Level | g broth used for dilut. | g water added | Theoret. Lactic | % Lactic | Theor. PO4 | % PO4 | Theor. NH3 | % NH3 | Theoret. Water | % Water | g dil broth used for extra c. |
|---|---|---|---|---|---|---|---|---|---|---|---|---|
| 6A | 100% | 10 | 0 | 55.39% | 53.14% | 3.27% | 3.52% | 2.56% | 2.55% | 28.70% | 28.83% | 8.01 |
| 6B | 98% | 10 | 0.21 | 54.28% | 53.18% | 3.20% | 3.56% | 2.51% | 2.49% | 30.17% | 30.24% | 8.02 |
| 6C | 95% | 10 | 0.51 | 52.62% | 51.32% | 3.11% | 3.40% | 2.43% | 2.48% | 32.16% | 32.28% | 7.99 |
| 6D | 93% | 10 | 0.75 | 51.51% | 51.11% | 3.04% | 3.37% | 2.38% | 2.33% | 33.67% | 33.73% | 8.03 |
| 6E | 90% | 10 | 1.12 | 49.85% | 48.76% | 2.94% | 2.90% | 2.30% | 2.32% | 35.88% | 36.27% | 8.02 |
| 6F | 80% | 10 | 2.52 | 44.31% | 43.30% | 2.62% | 3.15% | 2.05% | 1.97% | 43.05% | 43.14% | 8.03 |

| Sample | g lactic in | g PO4 in | g NH3 in | g water in | g solvent used | Solvent Phase ||||||
|---|---|---|---|---|---|---|---|---|---|---|---|
| | | | | | | g solvent out | % lactic | g lactic out | % lactic recovery | PO4 ppm | % PO4 | g PO4 |
| 6A | 4.257 | 0.282 | 0.204 | 2.309 | 32 | 34.48 | 8.04% | 2.772 | 65.13% | 279 | 0.0279% | 0.0096 |
| 6B | 4.265 | 0.286 | 0.200 | 2.425 | 32.03 | 34.33 | 8.05% | 2.764 | 64.80% | 252 | 0.0252% | 0.0087 |
| 6C | 4.100 | 0.272 | 0.198 | 2.579 | 32.05 | 34.28 | 7.57% | 2.595 | 63.29% | 261 | 0.0261% | 0.0089 |
| 6D | 4.104 | 0.271 | 0.187 | 2.709 | 32.04 | 34.35 | 7.57% | 2.600 | 63.36% | 254 | 0.0254% | 0.0087 |
| 6E | 3.911 | 0.233 | 0.186 | 2.909 | 32.01 | 34.15 | 7.03% | 2.401 | 61.39% | 196 | 0.0196% | 0.0067 |
| 6F | 3.477 | 0.253 | 0.158 | 3.464 | 32.02 | 34 | 6.35% | 2.159 | 62.09% | 198 | 0.0198% | 0.0067 |

| | Solvent Phase |||||||||
|---|---|---|---|---|---|---|---|---|---|
| Sample | % PO4 recov. | % NH3 | g NH3 | % NH3 recovery | % water | g water in* | g water out | g water picked up from aqueous | % change in water |
| 6A | 3.41% | 0.076% | 0.0262 | 12.83% | 5.81% | 1.92 | 2.0033 | 0.0833 | 4.16% |
| 6B | 3.03% | 0.066% | 0.0227 | 11.35% | 5.52% | 1.9218 | 1.8950 | −0.0268 | −1.41% |
| 6C | 3.29% | 0.056% | 0.0192 | 9.69% | 5.91% | 1.923 | 2.0259 | 0.1029 | 5.08% |
| 6D | 3.22% | 0.050% | 0.0172 | 9.18% | 6.02% | 1.9224 | 2.0679 | 0.1455 | 7.03% |
| 6E | 2.88% | 0.037% | 0.0126 | 6.79% | 6.08% | 1.9206 | 2.0763 | 0.1557 | 7.50% |
| 6F | 2.66% | 0.032% | 0.0109 | 6.88% | 6.35% | 1.9212 | 2.1590 | 0.2378 | 11.01% |

Figure 14:
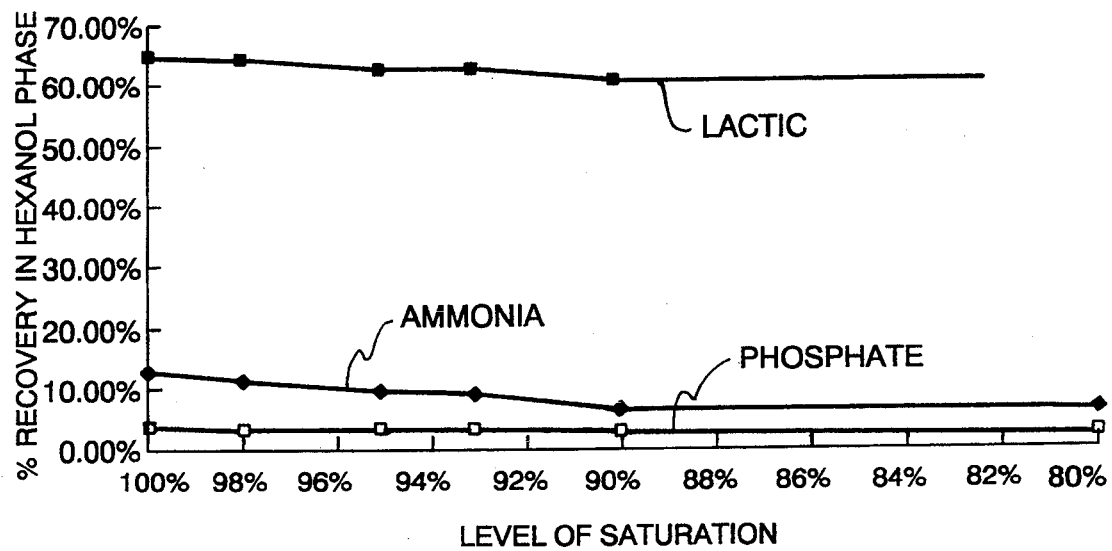
FIG. 14 is a graph of the percentage recovery in the solvent phase of various components at varying levels of broth saturation.

See FIG. 14.

EXAMPLE 7

Three cross-current extractions runs with a lactic acid solution were done with hexanol, 6% water, and the following acids: 0.7% phosphoric, 0.26% hydrochloric, and 0.46% sulfuric. The ratio of solvent to aqueous phases was 4:1.

Each time the precipitate dissolved, a dramatic decrease in pH was noted.

EXAMPLE 8

A concentrated fermentation broth containing lactic acid (65%) was acidulated with 75% phosphoric acid to a pH of 3.0. The acidulated suspension was clarified by filtration and a portion of the supernatant was subjected

TABLE 7

| | Hexanol Extraction with Different Acids |||||||||
|---|---|---|---|---|---|---|---|---|---|
| | g Solvent Phase | % Lactic | g Lactic | Cum g | % Lactic Acid Removed | pH | g raffinate | % lactic | g lactic remaining | % lactic remaining |
| 0.7% H3PO4; Extraction | | | | | | | | | | |
| 1 | 35.13 | 8.72 | 3.06 | 3.06 | 67.11% | — | | | | |
| 2 | 32.42 | 2.47 | 0.80 | 3.86 | 84.65% | — | | | | |
| 3 | 31.84 | 0.84 | 0.27 | 4.13 | 90.57% | 4.32 | | | | |
| 4 | 31.92 | 0.73 | 0.23 | 4.36 | 95.61% | 4.04 | | | | |
| 5 | 31.73 | 0.32 | 0.10 | 4.46 | 97.81% | 3.55 | | | | |
| 6 | 31.64 | 0.07 | 0.02 | 4.48 | 98.25% | 3 | 5.03 | 0.14% | 0.007 | 0.05% |
| 0.26% HCl; Extraction | | | | | | | | | | |
| 1 | 34.95 | 8.8 | 3.08 | 3.08 | 67.54% | — | | | | |
| 2 | 32.63 | 2.34 | 0.76 | 3.84 | 84.19% | — | | | | |
| 3 | 32.02 | 0.25 | 0.08 | 3.92 | 85.95% | 4.08 | | | | |
| 4 | 31.99 | 0.13 | 0.04 | 3.96 | 86.94% | 4.06 | | | | |
| 5 | 31.90 | 0.44 | 0.14 | 4.10 | 89.92% | 3.55 | | | | |
| 6 | 31.81 | 0.08 | 0.03 | 4.13 | 90.57% | 2.32 | 4.36 | 0.78% | 0.034 | 0.24% |
| 0.46% H2SO4 | | | | | | | | | | |
| 1 | 35.09 | 8.91 | 3.13 | 3.13 | 68.64% | 4.09 | | | | |
| 2 | 32.4 | 2.61 | 0.85 | 3.98 | 87.19% | 4.33 | | | | |
| 3 | 32 | 0.57 | 0.18 | 4.16 | 91.19% | 4.25 | | | | |
| 4 | 31.81 | 0.65 | 0.21 | 4.36 | 95.72% | 2.92 | | | | |
| 5 | 31.54 | 0.09 | 0.03 | 4.39 | 96.34% | 1.96 | | | | |
| 6 | 31.76 | 0.00003 | 0.00 | 4.39 | 96.34% | 1.75 | 4.68 | 0.07% | 0.003 | 0.02% |

Figure 15:
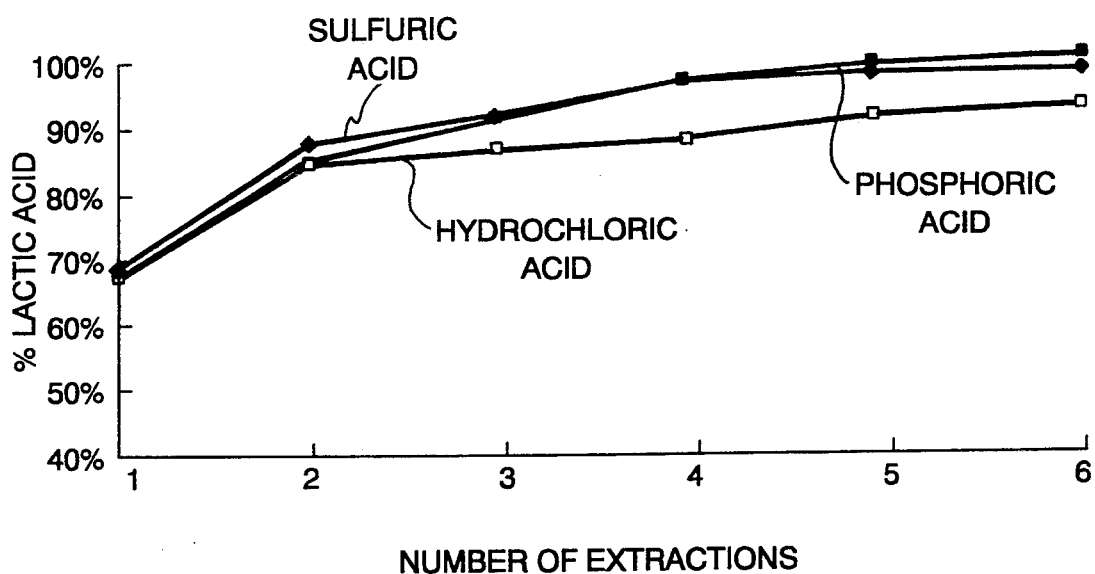
FIG. 15 is a graph of the percent lactic acid removed in extractions employing different acids.

See FIG. 15.

Precipitate formed with the phosphoric acid sample after stage 3 and redissolved after the fourth. Precipitate to a six by six counter-current extraction process.

(Mass-Transfer Operations, 3rd Ed., Robert E. Treybal, McGraw-Hill, 1955, p. 518.) The filtered, acidulated supernatant contained 55.39% lactic acid, 3.27% phosphate, 2.56% ammonia, and 28.7% water. The supernatant was extracted at a solvent to aqueous ratio of 4:1; the solvent contained hexanol, 0.7% phosphoric acid, and 7% water.

TABLE 8

| | Counter-Current Extraction of Broth | | | | | | | | | | |
|---|---|---|---|---|---|---|---|---|---|---|---|
| | Aqueous Broth Feed | Solvent In | Aqueous Out | Solvent out | Aqueous Wt Loss | Solvent Wt Gain | Final Aqueous | | | | |
| | | | | | | | % lactic | % PO4 | % NH3 | % Water | % Hexanol |
| Row 1; Stage | | | | | | | | | | | |
| 1 | 8.13 | 32.02 | 5.62 | 34.36 | 2.51 | 2.34 | — | — | — | — | — |
| 2 | 5.62 | 32.06 | 5.07 | 32.39 | 0.55 | 0.33 | — | — | — | — | — |
| 3 | 5.07 | 32.03 | 5.01 | 31.89 | 0.06 | −0.14 | — | — | — | — | — |
| 4 | 5.01 | 32.00 | 5.01 | 31.77 | −0.06 | −0.23 | — | — | — | — | — |
| 5 | 5.07 | 32.02 | 5.07 | 31.75 | 0 | −0.27 | — | — | — | — | — |
| 6 | 5.07 | 32.04 | 5.07 | 31.82 | 0 | −0.22 | 4.08% | 18.76% | 3.70% | 60.70% | 0.03% |
| Row 2; Stage | | | | | | | | | | | |
| 1 | 7.99 | 32.39 | 4.54 | 35.51 | 3.45 | 3.12 | — | — | — | — | — |
| 2 | 4.54 | 31.89 | 4.08 | 32.08 | 0.46 | 0.19 | — | — | — | — | — |
| 3 | 4.08 | 31.77 | 3.97 | 31.69 | 0.11 | −0.08 | — | — | — | — | — |
| 4 | 3.97 | 31.71 | 4.03 | 31.44 | −0.06 | −0.31 | — | — | — | — | — |
| 5 | 4.03 | 31.82 | 4.08 | 31.58 | −0.05 | −0.24 | — | — | — | — | — |
| 6 | 4.08 | 31.99 | 4.12 | 31.75 | −0.04 | −0.24 | 5.28% | 18.39% | 3.71% | 59.30% | 0.02% |
| Row 3; Stage | | | | | | | | | | | |
| 1 | 8.02 | 32.08 | 4.54 | 35.35 | 3.48 | 3.27 | — | — | — | — | — |
| 2 | 4.54 | 31.69 | 3.89 | 32.13 | 0.65 | 0.44 | — | — | — | — | — |
| 3 | 3.89 | 31.44 | 3.70 | 31.49 | 0.19 | 0.05 | — | — | — | — | — |
| 4 | 3.7 | 31.58 | 3.74 | 31.37 | −0.04 | −0.21 | — | — | — | — | — |
| 5 | 3.74 | 31.75 | 3.83 | 31.48 | −0.09 | −0.27 | — | — | — | — | — |
| 6 | 3.83 | 32.03 | 3.86 | 31.75 | −0.03 | −0.28 | 9.86% | 15.01% | 3.91% | 58.10% | 0.05% |

| | Final Solvent | | | | | | | |
|---|---|---|---|---|---|---|---|---|
| | % lactic | % PO4 | % NH3 | % Water | % Hexanol | g lactic in | g lactic out Solvent | g Lactic Out Aqueous |
| Row 1; Stage | | | | | | | | |
| 1 | 7.73% | 0.03% | 0.07% | 5.62% | — | 4.503 | 2.656 | — |
| 2 | — | — | — | — | — | — | — | — |
| 3 | — | — | — | — | — | — | — | — |
| 4 | — | — | — | — | — | — | — | — |
| 5 | — | — | — | — | — | — | — | — |
| 6 | — | — | — | — | — | — | — | 0.207 |
| Row 2; Stage | | | | | | | | |
| 1 | 10.55% | 0.04% | 0.13% | 6.04% | — | 4.426 | 3.746 | — |
| 2 | — | — | — | — | — | — | — | — |
| 3 | — | — | — | — | — | — | — | — |
| 4 | — | — | — | — | — | — | — | — |
| 5 | — | — | — | — | — | — | — | — |
| 6 | — | — | — | — | — | — | — | 0.218 |
| Row 3; Stage | | | | | | | | |
| 1 | 10.66% | 0.03% | 0.12% | 6.03% | — | 4.442 | 3.768 | — |
| 2 | — | — | — | — | — | — | — | — |
| 3 | — | — | — | — | — | — | — | — |
| 4 | — | — | — | — | — | — | — | — |
| 5 | — | — | — | — | — | — | — | — |
| 6 | — | — | — | — | — | — | — | 0.381 |

| | Aqueous Broth Feed | Solvent In | Aqueous Out | Solvent out | Aqueous Wt Loss | Solvent Wt Gain | Final Aqueous | | | | |
|---|---|---|---|---|---|---|---|---|---|---|---|
| | | | | | | | % lactic | % PO4 | % NH3 | % Water | % Hexanol |
| Row 4; Stage | | | | | | | | | | | |
| 1 | 8.02 | 32.13 | 4.36 | 35.59 | 3.66 | 3.46 | — | — | — | — | — |
| 2 | 4.36 | 31.49 | 3.72 | 31.96 | 0.64 | 0.47 | — | — | — | — | — |
| 3 | 3.72 | 31.37 | 3.53 | 31.72 | 0.19 | 0.35 | — | — | — | — | — |
| 4 | 3.53 | 31.48 | 3.52 | 31.3 | 0.01 | −0.18 | — | — | — | — | — |
| 5 | 3.52 | 31.75 | 3.72 | 31.29 | −0.2 | −0.46 | — | — | — | — | — |
| 6 | 3.72 | 32.05 | 3.98 | 31.83 | −0.26 | −0.22 | 9.40% | 14.42% | 3.83% | 58.40% | 0.03% |
| Row 5; Stage | | | | | | | | | | | |
| 1 | 8.00 | 31.96 | 4.68 | 35.09 | 3.32 | 3.13 | — | — | — | — | — |
| 2 | 4.68 | 31.72 | 3.80 | 32.07 | 0.88 | 0.35 | — | — | — | — | — |
| 3 | 3.80 | 31.30 | 3.77 | 31.06 | 0.03 | −0.24 | — | — | — | — | — |
| 4 | 3.77 | 31.29 | 3.37 | 31.25 | 0.40 | −0.04 | — | — | — | — | — |
| 5 | 3.37 | 31.83 | 3.67 | 31.51 | −0.30 | −0.32 | — | — | — | — | — |
| 6 | 3.67 | 32.08 | 3.63 | 31.61 | 0.04 | −0.47 | 10.16% | 14.45% | 3.96% | 58.00% | 0.03% |
| Row 6; Stage | | | | | | | | | | | |
| 1 | 8.02 | 32.07 | 4.39 | 35.49 | 3.63 | 3.42 | — | — | — | — | — |
| 2 | 4.39 | 31.06 | 3.85 | 31.56 | 0.54 | 0.5 | — | — | — | — | — |

TABLE 8-continued

Counter-Current Extraction of Broth

| | | | | | | | | | | |
|---|---|---|---|---|---|---|---|---|---|---|
| 3 | 3.85 | 31.25 | 3.45 | 31.32 | 0.40 | 0.07 | — | — | — | — |
| 4 | 3.45 | 31.51 | 3.40 | 31.42 | 0.05 | −0.09 | — | — | — | — |
| 5 | 3.40 | 31.61 | 3.45 | 31.35 | −0.05 | −0.26 | — | — | — | — |
| 6 | 3.45 | 32.02 | 3.59 | 31.80 | −0.14 | −0.22 | 12.94% | 12.13% | 4.12% | 56.10% | 0.03% |

| | Final Solvent | | | | | | | |
|---|---|---|---|---|---|---|---|---|
| | % lactic | % PO4 | % NH3 | % Water | % Hexanol | g lactic in | g lactic out Solvent | g Lactic Out Aqueous |
| Row 4; Stage | | | | | | | | |
| 1 | 11.10% | 0.04% | 0.16% | 6.04% | — | 4.442 | 3.950 | — |
| 2 | — | — | — | — | — | — | — | — |
| 3 | — | — | — | — | — | — | — | — |
| 4 | — | — | — | — | — | — | — | — |
| 5 | — | — | — | — | — | — | — | — |
| 6 | — | — | — | — | — | — | — | 0.374 |
| Row 5; Stage | | | | | | | | |
| 1 | 10.69% | 0.03% | 0.14% | 5.91% | — | 1.430 | 3.751 | — |
| 2 | — | — | — | — | — | — | — | — |
| 3 | — | — | — | — | — | — | — | — |
| 4 | — | — | — | — | — | — | — | — |
| 5 | — | — | — | — | — | — | — | — |
| 6 | — | — | — | — | — | — | — | 0.369 |
| Row 6; Stage | | | | | | | | |
| 1 | 11.51% | 0.04% | 0.36% | 6.08% | — | 4.441 | 4.085 | — |
| 2 | 3.58% | 0.00% | 0.12% | 4.55% | — | — | — | — |
| 3 | 1.79% | 0.00% | 0.02% | 4.43% | — | — | — | — |
| 4 | 1.08% | 0.00% | 0.02% | 4.75% | — | — | — | — |
| 5 | 0.68% | 0.03% | 0.01% | 4.71% | — | — | — | — |
| 6 | 0.74% | 0.03% | 0.01% | 5.06% | — | — | — | 0.465 |

EXAMPLE 9

A cross-current extraction was conducted to purify lactic acid. The organic phase comprised lactic acid 10.81%, water 8.08%, hexanol 78.43%, and phosphate 205 ppm, and the aqueous phase comprised lactic acid 19.09% and water 80.91%. A 10:1 organic/aqueous ratio was used.

TABLE 9

Cross-Current Lactic Acid Purification

| | | | | | Aqueous Layer Analysis | | | | % of | |
|---|---|---|---|---|---|---|---|---|---|---|
| Stage # | g Organic Phase In | g Organic Phase Out | g Aqueous Phase In | g Aqueous Phase Out | % Water | % Lactic | % Phos | mg Phos Aqueous | Total Phos | Cum % Phos Out |
| 1 | 30.06 | 30.71 | 3.07 | 2.36 | 72.9 | 21.04 | 0.179 | 4.215 | 68.40 | 68.4 |
| 2 | 30.71 | 30.48 | 3.01 | 3.11 | 75.94 | 21.38 | 0.065 | 2.022 | 32.81 | 101.21 |
| 3 | 30.48 | 30.21 | 3.02 | 3.14 | 76.01 | 21.29 | 0.022 | 0.703 | 11.41 | 112.62 |
| 4 | 30.21 | 29.89 | 3.08 | 3.22 | 76.78 | 20.61 | 0.012 | 0.399 | 6.48 | 119.1 |
| 5 | 29.89 | 29.64 | 3.03 | 3.17 | 77.79 | 20.73 | 0.002 | 0.060 | 0.98 | 120.08 |
| 6 | 29.64 | 29.4 | 3.02 | 3.11 | 77.15 | 20.31 | 0.000 | 0.000 | 0.00 | 120.08 |
| 7 | 29.4 | 29.15 | 3.07 | 3.22 | 76.88 | 19.89 | 0.000 | 0.000 | 0.00 | 120.08 |
| 8 | 29.15 | 28.94 | 3.13 | 3.22 | 77.21 | 19.82 | 0.000 | 0.000 | 0.00 | 120.08 |

Figure 16:
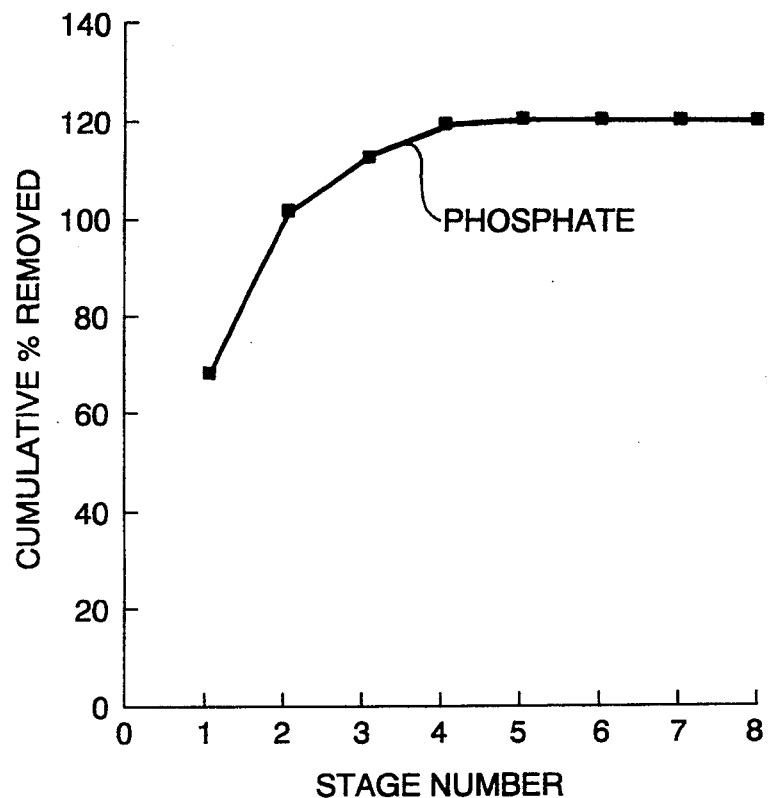
FIG. 16 is a graph of the percent lactic acid removed in a cross-current back extraction.

See FIG. 16.

EXAMPLE 10

To find the optimum aqueous lactic acid concentration for ion removal from lactic acid in hexanol, single 10:1 solvent/aqueous extractions were performed with concentrations of 18, 21, 23, 25, 27, and 30% lactic acid in the aqueous phase. The solvent phase was 9.73% lactic acid, 330 ppm PO4, 9.55% H2O, and 76.22% hexanol.

TABLE 10

| Theoretical Aqueous Conc. | Actual Aqueous Conc. | Change in Lactic Acid Conc. in Feed |
|---|---|---|
| 18% | 18.69% | −1.37% |
| 21% | 22.01% | +1.37% |
| 23% | 22.01% | +6.16% |
| 25% | 24.47% | +7.85% |
| 27% | 28.71% | +10.96% |
| 30% | 31.60% | +12.29% |

Figure 17:
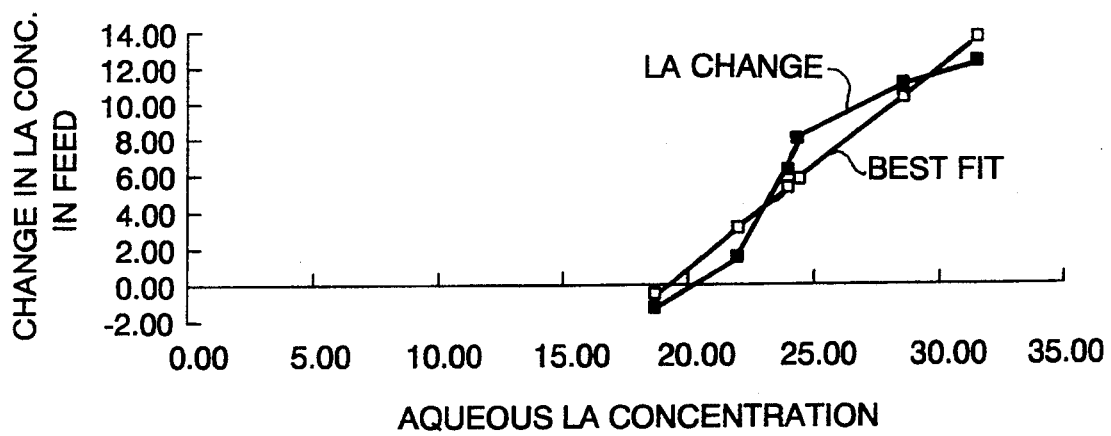
FIG. 17 is a graph of the change in lactic acid content of the feed vs. that of the aqueous phase for back extractions.

Using a best fit curve (see FIG. 17), 19% aqueous lactic acid should give little or no movement of lactic acid from solvent to aqueous phase during purification-/ion removal.

EXAMPLE 11

The effect of temperature on the back extraction of lactic acid from hexanol to water was tested. The original single phase in this experiment contained 18.31% (weight) lactic acid, 12.70% water, and 68.99% hexanol. Water was added at 20° C., 30° C., and 45° C.

TABLE 11

| | 20° C. | 30° C. | 45° C. |
|---|---|---|---|
| single phase (g) | 10.71 | 11.18 | 10.85 |
| water added to reach cloud point (g) | 0.3 | 0.32 | 0.39 |
| water excess (g) | 1.0 | 1.3 | 1.3 |
| Total (g) | 12.01 | 12.80 | 12.54 |

TABLE 12

| quantity of phases (measured) | 20° C. | 30° C. | 45° C. |
|---|---|---|---|
| aqueous (g) | 1.61 | 1.71 | 1.59 |
| organic (g) | 10.59 | 10.86 | 10.55 |

TABLE 13

Analysis of Phases

| | Aqueous | | | Organic | | | |
|---|---|---|---|---|---|---|---|
| | % lactic | % hex. | % water | % lactic | % hex. | % water | $K_s$* lactic |
| 20° C. | 27.29 | 3.76 | 68.95 | 14.19 | 72.93 | 12.88 | 0.520 |
| 30° C. | 27.27 | 4.33 | 68.40 | 14.70 | 72.33 | 12.97 | 0.539 |
| 45° C. | 26.90 | 4.13 | 68.97 | 14.63 | 72.36 | 13.01 | 0.544 |
| average | 27.15 | 4.07 | 68.78 | 14.51 | 72.52 | 12.95 | 0.534 |

*$K_2$ = distribution coefficient = $c_s/c_w$, where $c_s$ = concentration of lactic acid in aqueous phase and $c_w$ = concentration of lactic acid in solvent phase.

TABLE 14

Total Composition

| | % lactic | % hexanol | % water |
|---|---|---|---|
| 20° C. | 15.85 | 63.88 | 20.28 |
| 30° C. | 16.05 | 63.34 | 20.61 |
| 45° C. | 16.23 | 63.43 | 20.35 |

Thus, there appeared to be no benefit in extraction efficiency from increasing the extraction temperature from 20° C. to 45° C. To the extent any trend could be discerned, increasing temperature appeared to have an adverse effect.

EXAMPLE 12

First stage back extractions were performed on a lactic acid solution (11.95% lactic acid, 10.3% water, and 77.75% hexanol) with water at 4:1, 6:1, 8:1, and 10:1 organic to aqueous ratios. The lactic acid concentration was measured in the aqueous phase and the percent lactic acid removal was calculated for each of the various ratios of organic to aqueous phase. From this recovery, an estimation of the number of stages required to remove 97% of the lactic acid was made. Ratios of 4:1, 6:1, and 8:1 require 6, 9, and 11 stages respectively.

TABLE 15A

| | g solvent | solvent % lactic | solvent in g lactic | g water | g aqueous out | g solvent out | aqueous % lactic | aqueous g lactic | % lactic removal |
|---|---|---|---|---|---|---|---|---|---|
| 4:1 | 4 | 11.95% | 0.48 | 1 | 1.35 | 3.65 | 14.28% | 0.193 | 40.33% |
| 6:1 | 6.01 | 11.95% | 0.72 | 1 | 1.4 | 5.58 | 16.07% | 0.225 | 31.33% |
| 8:1 | 8 | 11.95% | 0.96 | 1.01 | 1.43 | 7.6 | 17.64% | 0.252 | 26.39% |
| 10:1 | 10 | 11.95% | 1.20 | 1.01 | 1.53 | 9.49 | 18.34% | 0.281 | 23.48% |

TABLE 15B

| 4:1 extraction | g lactic | % removal | g lactic removed | g lactic cum | % removed cum |
|---|---|---|---|---|---|
| 1 | 0.478 | 40.33% | 0.193 | 0.193 | 40.38% |
| 2 | 0.285 | 40.33% | 0.115 | 0.308 | 64.42% |
| 3 | 0.170 | 40.33% | 0.069 | 0.377 | 78.77% |
| 4 | 0.101 | 40.33% | 0.041 | 0.417 | 87.33% |
| 5 | 0.061 | 40.33% | 0.024 | 0.442 | 92.44% |
| 6 | 0.036 | 40.33% | 0.015 | 0.456 | 95.49% |

TABLE 15C

| 6:1 extraction | g lactic | % removal | g lactic removed | g lactic cum | % removed cum |
|---|---|---|---|---|---|
| 1 | 0.718 | 31.33% | 0.225 | 0.225 | 31.34% |
| 2 | 0.493 | 31.33% | 0.155 | 0.380 | 52.86% |
| 3 | 0.339 | 31.33% | 0.106 | 0.486 | 67.63% |
| 4 | 0.233 | 31.33% | 0.073 | 0.558 | 77.78% |
| 5 | 0.160 | 31.33% | 0.050 | 0.609 | 84.75% |
| 6 | 0.110 | 31.33% | 0.034 | 0.643 | 89.54% |
| 7 | 0.075 | 31.33% | 0.024 | 0.666 | 92.82% |
| 8 | 0.052 | 31.33% | 0.016 | 0.683 | 95.08% |
| 9 | 0.036 | 31.33% | 0.011 | 0.694 | 96.63% |

TABLE 15D

| 8:1 extraction | g lactic | % removal | g lactic removed | g lactic cum | % removed cum |
|---|---|---|---|---|---|
| 1 | 0.956 | 26.39% | 0.252 | 0.252 | 26.36% |
| 2 | 0.704 | 26.39% | 0.186 | 0.438 | 45.79% |
| 3 | 0.518 | 26.39% | 0.137 | 0.574 | 60.08% |
| 4 | 0.381 | 26.39% | 0.101 | 0.675 | 70.61% |
| 5 | 0.281 | 26.39% | 0.074 | 0.749 | 78.36% |
| 6 | 0.207 | 26.39% | 0.055 | 0.804 | 84.06% |
| 7 | 0.152 | 26.39% | 0.040 | 0.844 | 88.26% |
| 8 | 0.112 | 26.39% | 0.030 | 0.873 | 91.35% |
| 9 | 0.082 | 26.39% | 0.022 | 0.895 | 93.62% |
| 10 | 0.061 | 26.39% | 0.016 | 0.911 | 95.30% |
| 11 | 0.045 | 26.39% | 0.012 | 0.923 | 96.53% |

Figure 18:
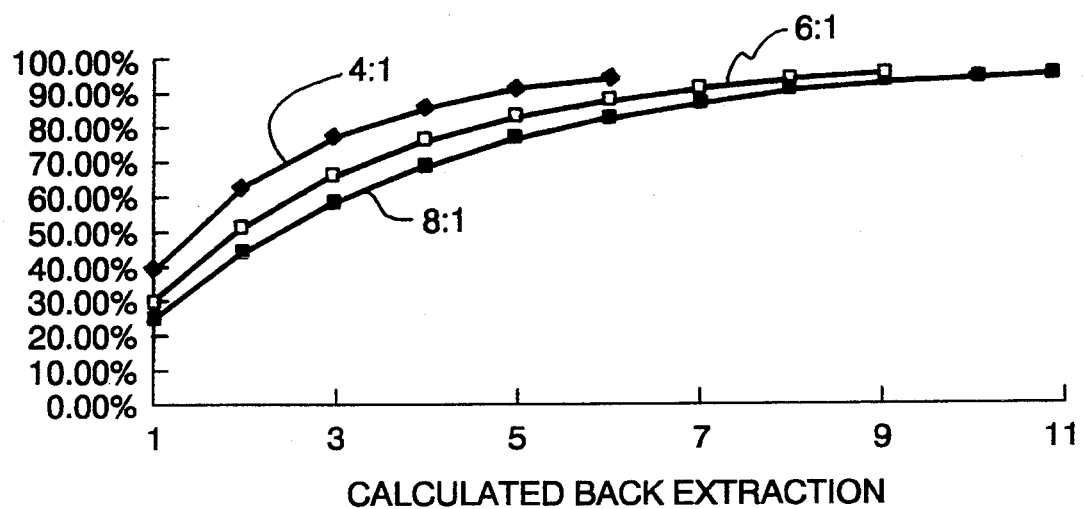
FIG. 18 is a graph showing calculated numbers of back extraction stages required to reach a given level of lactic acid recovery.

See FIG. 18.

EXAMPLE 12

Figure 19:
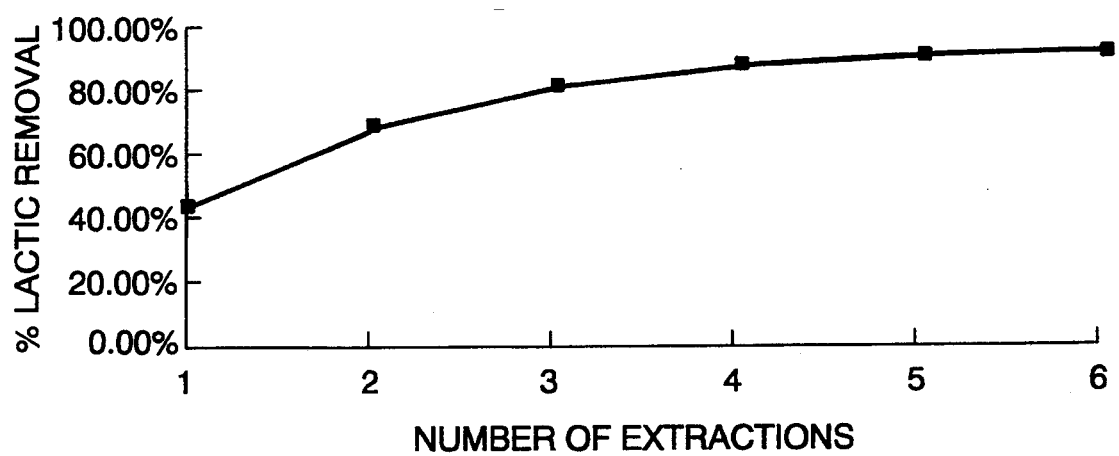
FIG. 19 is a graph showing the percent lactic acid recovery after each of several cross-current back extractions.

A cross-current six-stage back extraction was performed with a 4:1 solvent to aqueous ratio. The solvent composition was 10.82% lactic acid, 10.5% water, and 78.68% hexanol. 98.62% of the lactic acid was recovered in the aqueous stream. See FIG. 19.

EXAMPLE 14

A counter-current six-stage back extraction was performed with a 4:1 solvent to aqueous ratio. The solvent comprised 10.5% water, 10.82% lactic acid, and 78.62% hexanol. 16.04% of the lactic acid entering row 6 was left with the solvent stream. The final aqueous stream comprised 20.06% lactic acid and 0.7% hexanol. The final solvent stream comprised 2.03% lactic acid and 7.83% water.

The preceding description of specific embodiments of the present invention is not intended to be a complete list of every possible embodiment of the invention. Persons who are skilled in this field will recognize that modifications can be made to the specific embodiments described here that would be within the scope of the present invention.

We claim:

1. A process for the extraction of an organic acid from an aqueous solution thereof which comprises contacting an aqueous solution of an organic acid, wherein the organic acid is selected from the group consisting of mono, di, and tricarboxylic acids having from 3-8 carbon atoms, with a mixture consisting essentially of (a) water, (b) a mineral acid in a quantity effective to maintain the pH of the mixture between about 1.0 and about 4.5, and (c) an oxygenated solvent which has limited miscibility with water and the aqueous solution, the oxygenated solvent having from 6 to 8 carbon atoms and having at least one functional group selected from the group consisting of hydroxyl, ester, keto, ether, carbonyl, and amido.

2. The process of claim 1, where the aqueous solution of organic acid is substantially saturated with respect to at least one electrolyte selected from the group consisting of $MHSO_4$, $M_2SO_4$, $M_3PO_4$, $M_2HPO_4$, $MH_2PO_4$, and $MNO_3$, where M is selected from the group consisting of Na, $NH_4$, and K.

3. The process of claim 1 where the oxygenated solvent is hexanol.

4. The process of claim 1, where the contacting is performed in a mixer-settler apparatus.

5. A process for recovering an organic acid, including the steps of:

providing an aqueous feed containing an organic acid and impurities, wherein the organic acid is selected from the group consisting of mono, di, and tricarboxylic acids having from 3–8 carbon atoms;

clarifying the aqueous feed to remove at least a substantial portion of the impurities therein, producing a clarified feed;

acidulating the clarified liquid feed by adding a quantity of a mineral acid effective to lower the pH of the feed to between about 1.0 and about 4.5, producing an acidulated feed which is substantially saturated with respect to at least one electrolyte selected from the group consisting of $MHSO_4$, $M_2SO_4$, $M_3PO_4$, $M_2HPO_4$, $MH_2PO_4$, and $MNO_3$, where M is selected from the group consisting of Na, $NH_4$, and K;

extracting the acidulated feed with an extraction mixture which consists essentially of (a) water, (b) a mineral acid, in a quantity effective to maintain the pH of the feed between about 1.0 and about 4.5, and (c) an oxygenated solvent which has limited miscibility with water and the acidulated feed, the oxygenated solvent having from 5 to 12 carbon atoms and having at least one functional group selected from the group consisting of hydroxyl, ester, keto, ether, carbonyl, and amido, with the extraction producing a solvent extract and a first raffinate; and back extracting the solvent extract with an aqueous liquid, thereby producing an organic acid-rich aqueous extract and an organic acid-depleted solvent raffinate.

6. The process of claim 5, where the extraction of the acidulated feed is performed in a mixer-settler apparatus.

7. The process of claim 5, where the back extraction is performed in a mixer-settler apparatus.

8. The process of claim 5, where the oxygenated solvent has from 6 to 8 carbon atoms.

9. The process of claim 5, where the oxygenated solvent is hexanol.

10. The process of claim 5, where the ratio of the extraction mixture to the acidulated feed is between about 3/1 and about 6/1 by weight.

11. The process of claim 5, where the extraction mixture is substantially saturated with water.

12. The process of claim 5, further including the steps of:

concentrating the organic acid-rich aqueous extract by removing water; and decolorizing the extract to remove at least a portion of the impurities remaining therein.

13. The process of claim 5, further including the steps of:

recovering solvent from the first raffinate by stripping solvent therefrom; and recycling the recovered solvent for use in extracting the acidulated feed.

14. The process of claim 13, further including the steps of:

maintaining the pH of the acidulated feed during the extraction at a level effective to prevent substantial precipitation of phosphate, sulfate, nitrate, and chloride salts during the extraction; and recovering phosphate, sulfate, nitrate, or chloride salts from the first raffinate by evaporation after the solvent is stripped therefrom.

15. The process of claim 5, further including the steps of:

crystallizing a phosphate, sulfate, or nitrate salt from the acidulated feed;

washing the crystallized salt with an aqueous liquid; and drying the washed, crystallized salt.

16. The process of claim 5, further including the steps of:

filtering the aqueous feed to remove undesirable impurities;

concentrating the feed by removing a portion of the water therein; and decolorizing the feed by contacting it with a decolorizing agent;

with the filtering, concentrating, and decolorizing of the feed being done before the feed is acidulated.

17. The process of claim 16, where the decolorizing agent is selected from the group consisting of granular carbon, powdered carbon, and decolorizing resin.

18. The process of claim 5, further including the step of:

after extracting the acidulated feed with the extraction mixture of water, mineral acid, and oxygenated solvent, and before back extracting the solvent extract with the aqueous liquid, performing an additional extraction in which an aqueous solution which contains a quantity of the organic acid is used as the extractant of the solvent extract from the first extraction step, thereby producing a second raffinate and a purified solvent extract, with the latter subsequently being back extracted as specified in claim 5.

19. The process of claim 5, where at least 20% by weight of the total organic acid values in the aqueous feed are present in the form of alkali salts of the organic acid, and where the concentration of organic acid in the feed immediately prior to acidulation is greater than about 30% by weight.

20. A process for recovering lactic acid, including the steps of:

providing an aqueous feed containing lactic acid and impurities;

clarifying the aqueous feed to remove at least a substantial portion of the impurities therein, producing a clarified feed;

acidulating the clarified feed by adding a quantity of a mineral acid effective to lower the pH of the feed to between about 1.0 and about 4.5, producing an acidulated feed which is substantially saturated with respect to at least one electrolyte selected from the group consisting of $MHSO_4$, $M_2SO_4$, $M_3PO_4$, $M_2HPO_4$, $MH_2PO_4$, and $MNO_3$, where M is selected from the group consisting of Na, $NH_4$, and K;

extracting the acidulated feed with an extraction mixture which consists essentially of (a) water, (b) a mineral acid, in a quantity effective to maintain the pH of the feed between about 1.0 and about 4.5, and (c) hexanol, with the extraction producing a hexanol extract and a first raffinate; and back extracting the hexanol extract with an aqueous liquid, thereby producing a lactic acid-rich aqueous extract and a lactic acid-depleted hexanol raffinate.

21. The process of claim 20, where the extraction of the acidulated feed is performed in a mixer-settler apparatus.

22. The process of claim 20, where the back extraction is performed in a mixer-settler apparatus.

23. The process of claim 20, where the ratio of the extraction mixture to the acidulated feed is between about 3/1 and about 6/1 by weight.

24. The process of claim 20, where the extraction mixture is substantially saturated with water.

25. The process of claim 20, further including the steps of:
concentrating the lactic acid-rich aqueous extract by removing water; and
decolorizing the extract to remove at least a portion of the impurities remaining therein.

26. The process of claim 20, further including the steps of:
recovering hexanol from the first raffinate by stripping hexanol therefrom; and
recycling the recovered hexanol for use in extracting the acidulated feed.

27. The process of claim 26, further including the steps of:
maintaining the pH of the acidulated feed during the extraction at a level effective to prevent substantial precipitation of phosphate, sulfate, and nitrate salts during the extraction; and
recovering phosphate, sulfate, or nitrate salts from the first raffinate by evaporation after the solvent is stripped therefrom.

28. The process of claim 20, further including the steps of:
crystallizing a phosphate, sulfate, or nitrate salt from the acidulated feed;
washing the crystallized salt with an aqueous liquid; and
drying the washed, crystallized salt.

29. The process of claim 20, further including the steps of:
filtering the aqueous feed to remove undesirable impurities;
concentrating the feed by removing a portion of the water therein; and
decolorizing the feed by contacting it with a decolorizing agent;
with the filtering, concentrating, and decolorizing of the feed being done before the feed is acidulated.

30. The process of claim 29, where the decolorizing agent is selected from the group consisting of granular carbon, powdered carbon, and decolorizing resin.

31. The process of claim 20, further including the step of:
after extracting the acidulated feed with the extraction mixture of water, mineral acid, and hexanol, and before back extracting the hexanol extract with the aqueous liquid, performing an additional extraction in which an aqueous solution which contains a quantity of lactic acid is used as the extractant of the hexanol extract from the first extraction step, thereby producing a second raffinate and a purified hexanol extract, with the latter subsequently being back extracted as specified in claim 20.

32. The process of claim 20, where at least 20% by weight of the total lactic acid values in the aqueous feed are present in the form of alkali lactates, and where the concentration of lactic acid in the feed immediately prior to acidulation is greater than about 30% by weight.

33. A process for recovering lactic acid, including the steps of:
providing an aqueous feed containing lactic acid and impurities;
clarifying the aqueous feed to remove at least a substantial portion of the impurities therein, producing a clarified feed;
concentrating the feed by removing a portion of the water therein;
decolorizing the feed by contacting it with a decolorizing agent;
acidulating the clarified feed by adding a quantity of a mineral acid effective to lower the pH of the feed to between about 1.0 and about 4.5, producing an acidulated feed which is substantially saturated with respect to at least one electrolyte selected from the group consisting of $MHSO_4$, $M_2SO_4$, $M_3PO_4$, $M_2HPO_4$, $MH_2PO_4$, and $MNO_3$, where M is selected from the group consisting of Na, $NH_4$, and K;
extracting the acidulated feed with an extraction mixture which consists essentially of (a) water, (b) a mineral acid, in a quantity effective to maintain the pH of the feed between about 1.0 and about 4.5, and (c) hexanol, with the extraction producing a first hexanol extract and a first raffinate;
extracting the first hexanol extract with an aqueous lactic acid solution, thereby producing a second raffinate and a purified hexanol extract;
back extracting the purified hexanol extract with an aqueous liquid, thereby producing a lactic acid-rich aqueous extract and a lactic acid-depleted hexanol raffinate;
recovering hexanol from the first raffinate by stripping hexanol therefrom;
recycling the recovered hexanol for use in extracting the acidulated feed;
concentrating the lactic acid-rich aqueous extract by removing water; and
carbon-treating the concentrated extract to remove at least a portion of the impurities remaining therein.

* * * * *

UNITED STATES PATENT AND TRADEMARK OFFICE
CERTIFICATE OF CORRECTION

PATENT NO.   : 5,426,219
DATED        : June 20, 1995
INVENTOR(S)  : William F. Lehnhardt et al It is certified that error appears in the above-indentified patent and that said Letters Patent is hereby corrected as shown below:

Column 6, line 5, "$H_3, PO_4$" should be --$H_3PO_4$--.

Column 22, line 30, "EXAMPLE 12" should be --EXAMPLE 13--.

Signed and Sealed this

Twenty-first Day of November, 1995

Attest:

BRUCE LEHMAN

*Attesting Officer*     Commissioner of Patents and Trademarks